(12) United States Patent
Lubock et al.

(10) Patent No.: US 7,651,467 B2
(45) Date of Patent: Jan. 26, 2010

(54) DILATION DEVICES AND METHODS FOR REMOVING TISSUE SPECIMENS

(75) Inventors: Paul Lubock, Laguna Niguel, CA (US); Richard L. Quick, Mission Viejo, CA (US)

(73) Assignee: Senorx, Inc, Irvine, CA (US)

( * ) Notice: Subject to any disclaimer, the term of this patent is extended or adjusted under 35 U.S.C. 154(b) by 121 days.

(21) Appl. No.: 10/933,182

(22) Filed: Sep. 2, 2004

(65) Prior Publication Data

US 2005/0038462 A1 Feb. 17, 2005

Related U.S. Application Data

(63) Continuation of application No. 09/916,937, filed on Jul. 27, 2001, now Pat. No. 6,997,885.

(51) Int. Cl.
*A61B 10/00* (2006.01)
*A61M 29/00* (2006.01)
*A61B 18/18* (2006.01)

(52) U.S. Cl. .................. 600/567; 600/564; 604/104; 606/45

(58) Field of Classification Search .......... 600/562, 600/564, 567; 606/167, 170, 174, 190, 198, 606/205, 207–208; 604/96.01, 104–107, 604/164.01, 164.03, 164.1, 219, 227, 272
See application file for complete search history.

(56) References Cited

U.S. PATENT DOCUMENTS

| | | | |
|---|---|---|---|
| 2,032,860 A | 3/1936 | Wappler et al. |
| 2,192,270 A | 3/1940 | McGowan |
| 3,805,791 A | 4/1974 | Seuberth et al. |
| 3,844,272 A | 10/1974 | Banko |
| 3,945,375 A | 3/1976 | Banko et al. |
| 3,955,578 A | 5/1976 | Chamness et al. |
| 4,007,732 A | 2/1977 | Kvavie et al. |
| 4,202,338 A | 5/1980 | Bitroff |
| 4,243,048 A | 1/1981 | Griffin |
| 4,294,254 A | 10/1981 | Chamness |
| 4,311,143 A | 1/1982 | Komiya |
| 4,362,160 A | 12/1982 | Hiltebrandt |

(Continued)

FOREIGN PATENT DOCUMENTS

DE 19528440 8/1995

(Continued)

*Primary Examiner*—Max Hindenburg
*Assistant Examiner*—H. Q. Nguyen
(74) *Attorney, Agent, or Firm*—Edward J. Lynch

(57) ABSTRACT

The invention provides devices and methods for use in removing tissue samples from within a patient's body. The devices include instruments having shafts for cutting a path to a tissue mass, and an inflatable balloon or balloons attached to the shaft effective to dilate the path upon inflation in order to aid in the removal of tissue masses from within the body of a patient. The devices also include instruments having dilation plates that may be inserted into a path leading to a tissue mass to be removed, and the plates separated effective to dilate the path to aid in the removal of tissue masses. Methods include inserting a device into a path leading to a tissue mass, and inflating a balloon or separating plates, thereby widening the path, and removing the tissue mass. Such devices and methods find use, for example, in biopsy and in lumpectomy procedures.

1 Claim, 22 Drawing Sheets

U.S. PATENT DOCUMENTS

| | | |
|---|---|---|
| 4,425,908 A | 1/1984 | Simon |
| 4,503,855 A | 3/1985 | Maslanka |
| 4,565,200 A | 1/1986 | Cosman |
| 4,576,162 A | 3/1986 | McCorkle |
| 4,592,356 A | 6/1986 | Gutierrez |
| 4,611,594 A | 9/1986 | Grayhack et al. |
| 4,616,656 A | 10/1986 | Nicholson et al. |
| 4,638,802 A | 1/1987 | Okada |
| 4,682,606 A | 7/1987 | DeCaprio |
| 4,718,419 A | 1/1988 | Okada |
| 4,724,836 A | 2/1988 | Okada |
| 4,774,948 A | 10/1988 | Markham |
| 4,909,250 A | 3/1990 | Smith |
| 4,966,583 A | 10/1990 | Debbas |
| 5,007,908 A | 4/1991 | Rydell |
| 5,024,617 A | 6/1991 | Karpiel |
| 5,035,696 A | 7/1991 | Rydell |
| 5,037,379 A | 8/1991 | Clayman et al. |
| 5,047,027 A | 9/1991 | Rydell |
| 5,059,197 A | 10/1991 | Urie et al. |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| 5,085,659 A | 2/1992 | Rydell |
| 5,100,423 A | 3/1992 | Fearnot |
| RE33,925 E | 5/1992 | Bales et al. |
| 5,111,828 A | 5/1992 | Kornberg et al. |
| 5,133,359 A | 7/1992 | Kedem |
| RE34,056 E | 9/1992 | Lindgren et al. |
| 5,147,307 A | 9/1992 | Gluck |
| 5,158,084 A | 10/1992 | Ghiatas |
| 5,158,561 A | 10/1992 | Rydell et al. |
| 5,163,938 A | 11/1992 | Kambara et al. |
| 5,192,270 A | 3/1993 | Carswell, Jr. |
| 5,196,007 A | 3/1993 | Ellman et al. |
| 5,201,732 A | 4/1993 | Parins et al. |
| 5,201,741 A | 4/1993 | Dulebohn |
| 5,207,686 A | 5/1993 | Dolgin |
| 5,215,521 A | 6/1993 | Cochran et al. |
| 5,217,458 A | 6/1993 | Parins |
| 5,221,269 A | 6/1993 | Miller et al. |
| 5,224,488 A | 7/1993 | Neuffer |
| 5,234,426 A | 8/1993 | Rank et al. |
| 5,281,218 A | 1/1994 | Imran |
| 5,295,990 A | 3/1994 | Levin |
| 5,304,176 A | 4/1994 | Phillips |
| 5,312,400 A | 5/1994 | Bales et al. |
| 5,318,564 A | 6/1994 | Eggers |
| 5,323,768 A | 6/1994 | Saito et al. |
| 5,324,288 A | 6/1994 | Billings et al. |
| 5,335,671 A | 8/1994 | Clement |
| 5,337,754 A | 8/1994 | Heaven et al. |
| 5,344,420 A | 9/1994 | Hilal et al. |
| 5,353,804 A | 10/1994 | Kornberg et al. |
| 5,370,647 A | 12/1994 | Graber et al. |
| 5,374,188 A | 12/1994 | Frank et al. |
| 5,376,094 A | 12/1994 | Kline |
| 5,380,321 A | 1/1995 | Yoon |
| 5,395,312 A | 3/1995 | Desai |
| 5,395,319 A | 3/1995 | Hirsh et al. |
| 5,397,320 A | 3/1995 | Essig et al. |
| 5,403,310 A | 4/1995 | Fisher |
| 5,409,004 A | 4/1995 | Sloan |
| 5,415,656 A | 5/1995 | Tihon et al. |
| 5,417,687 A | 5/1995 | Nardella et al. |
| 5,417,697 A | 5/1995 | Wilk et al. |
| 5,423,814 A | 6/1995 | Zhu et al. |
| 5,431,649 A | 7/1995 | Mulier et al. |
| 5,437,665 A | 8/1995 | Munro |
| 5,441,503 A | 8/1995 | Considine et al. |
| 5,449,382 A | 9/1995 | Dayton |
| 5,454,365 A | 10/1995 | Bonutti |
| 5,462,553 A | 10/1995 | Dolgin |
| 5,470,308 A | 11/1995 | Edwards et al. |
| 5,484,436 A | 1/1996 | Eggers et al. |
| 5,487,385 A | 1/1996 | Avitall |
| 5,488,958 A | 2/1996 | Topel et al. |
| 5,501,654 A | 3/1996 | Failla et al. |
| 5,507,743 A | 4/1996 | Edwards et al. |
| 5,509,916 A | 4/1996 | Taylor |
| 5,526,822 A | 6/1996 | Burbank et al. |
| 5,527,331 A | 6/1996 | Kresch et al. |
| 5,542,948 A | 8/1996 | Weaver et al. |
| 5,554,159 A | 9/1996 | Fischer |
| 5,562,102 A * | 10/1996 | Taylor ........................ 600/564 |
| 5,578,030 A | 11/1996 | Levin |
| 5,578,031 A | 11/1996 | Wilk et al. |
| 5,593,418 A | 1/1997 | Mollenauer |
| 5,595,185 A | 1/1997 | Erlich et al. |
| 5,607,389 A | 3/1997 | Edwards et al. |
| 5,611,803 A | 3/1997 | Heaven et al. |
| 5,643,282 A | 7/1997 | Kieturakis |
| 5,649,547 A | 7/1997 | Ritchart et al. |
| 5,653,718 A | 8/1997 | Yoon |
| 5,665,085 A | 9/1997 | Nardella |
| 5,674,184 A | 10/1997 | Hassler, Jr. |
| 5,683,384 A | 11/1997 | Gough et al. |
| 5,687,739 A | 11/1997 | McPherson et al. |
| 5,700,273 A | 12/1997 | Buelna et al. |
| 5,715,825 A | 2/1998 | Crowley |
| 5,720,763 A | 2/1998 | Tovey |
| 5,730,726 A | 3/1998 | Klingenstein et al. |
| 5,735,847 A | 4/1998 | Gough et al. |
| 5,741,225 A | 4/1998 | Lax et al. |
| 5,743,906 A | 4/1998 | Parins et al. |
| 5,749,887 A | 5/1998 | Heske et al. |
| 5,752,972 A | 5/1998 | Hoogeboom |
| 5,755,697 A | 5/1998 | Jones et al. |
| 5,766,163 A | 6/1998 | Mueller et al. |
| 5,769,086 A | 6/1998 | Richart et al. |
| 5,769,794 A | 6/1998 | Conlan et al. |
| 5,772,660 A | 6/1998 | Young et al. |
| 5,775,333 A | 7/1998 | Burbank et al. |
| 5,782,764 A | 7/1998 | Werne |
| 5,782,775 A | 7/1998 | Milliman et al. |
| 5,788,709 A | 8/1998 | Riek et al. |
| 5,794,626 A | 8/1998 | Kieturakis |
| 5,795,308 A | 8/1998 | Russin |
| 5,797,907 A | 8/1998 | Clement |
| 5,800,378 A | 9/1998 | Edwards et al. |
| 5,800,445 A | 9/1998 | Ratcliff et al. |
| 5,810,806 A | 9/1998 | Ritchart et al. |
| 5,814,044 A | 9/1998 | Hooven |
| 5,827,268 A | 10/1998 | Laufer |
| 5,848,978 A | 12/1998 | Cecchi |
| 5,853,366 A | 12/1998 | Dowlatshahi |
| 5,857,981 A | 1/1999 | Bucalo et al. |
| 5,857,982 A | 1/1999 | Milliman et al. |
| 5,868,740 A | 2/1999 | LeVeen et al. |
| 5,876,340 A | 3/1999 | Tu et al. |
| 5,902,272 A | 5/1999 | Eggers et al. |
| 5,913,857 A | 6/1999 | Ritchart et al. |
| 5,925,044 A | 7/1999 | Hofmann et al. |
| 5,928,164 A | 7/1999 | Burbank et al. |
| 5,947,964 A | 9/1999 | Eggers et al. |
| 5,954,670 A | 9/1999 | Baker |
| 5,961,458 A | 10/1999 | Carroll |
| 5,964,716 A | 10/1999 | Gregoire et al. |
| 5,972,002 A | 10/1999 | Bark et al. |
| 5,980,469 A | 11/1999 | Burbank et al. |
| 5,984,919 A | 11/1999 | Hilal et al. |
| 6,004,269 A | 12/1999 | Crowley et al. |
| 6,032,673 A | 3/2000 | Savage et al. |

| | | | | | | |
|---|---|---|---|---|---|---|
| 6,056,700 | A | 5/2000 | Burney et al. | GB | 2311468 | 2/1997 |
| 6,063,082 | A | 5/2000 | DeVore et al. | WO | 9307811 | 4/1983 |
| 6,161,034 | A | 12/2000 | Burbank et al. | WO | 9735522 | 10/1992 |
| 6,312,429 | B1 | 11/2001 | Burbank et al. | WO | 9313718 | 7/1993 |
| 6,454,727 | B1 | 9/2002 | Burbank et al. | WO | 9401536 | 7/1994 |
| 6,482,178 | B1 | 11/2002 | Andrews et al. | WO | 9401537 | 7/1994 |
| 6,494,881 | B1 | 12/2002 | Bales et al. | WO | 9427670 | 12/1994 |
| 6,514,248 | B1 | 2/2003 | Eggers et al. | WO | 9502370 | 1/1995 |
| 6,540,695 | B1 | 4/2003 | Burbank et al. | WO | 9502371 | 1/1995 |
| 6,589,252 | B2 * | 7/2003 | McGuckin, Jr. ............. 606/114 | WO | 9503843 | 2/1995 |
| 6,689,145 | B2 | 2/2004 | Lee et al. | WO | 9510317 | 4/1995 |
| 6,712,775 | B2 | 3/2004 | Burbank et al. | WO | 9713460 | 4/1997 |
| 6,800,084 | B2 * | 10/2004 | Davison et al. ............. 606/198 | WO | 97/29702 A1 | 8/1997 |
| 2003/0004407 | A1 | 1/2003 | Carroll et al. | WO | 9806346 | 2/1998 |
| 2003/0083656 | A1 * | 5/2003 | Morrison et al. ............... 606/45 | WO | 9808441 | 3/1998 |
| 2003/0093112 | A1 * | 5/2003 | Addis ......................... 606/200 | WO | 9824372 | 6/1998 |
| | | | | WO | 9904704 | 2/1999 |
| | | FOREIGN PATENT DOCUMENTS | | WO | 9944506 | 9/1999 |
| EP | | 0472368 | 8/1991 | WO | 0016697 | 3/2000 |
| EP | | 0601709 | 6/1994 | WO | WO 00/12009 | 3/2000 |
| EP | | 0667126 | 8/1995 | WO | WO 00/74561 | 12/2000 |
| EP | | 0797957 | 1/1997 | WO | WO 01/05320 | 1/2001 |
| EP | | 0769 281 | 4/1997 | WO | WO 02/22023 | 3/2002 |
| EP | | 0858774 A2 | 8/1998 | WO | WO 2005/063126 | 7/2005 |
| EP | | 0 970 658 | 1/2001 | | | |

* cited by examiner

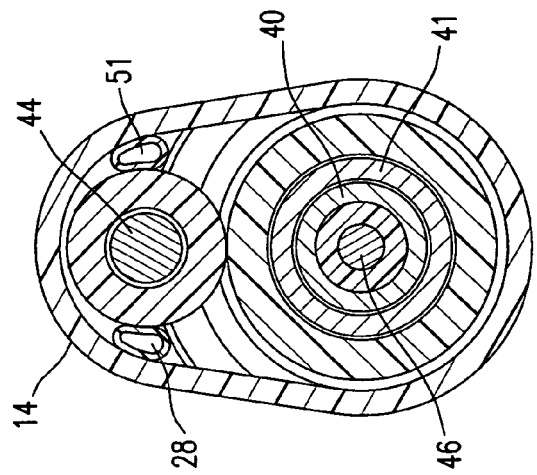
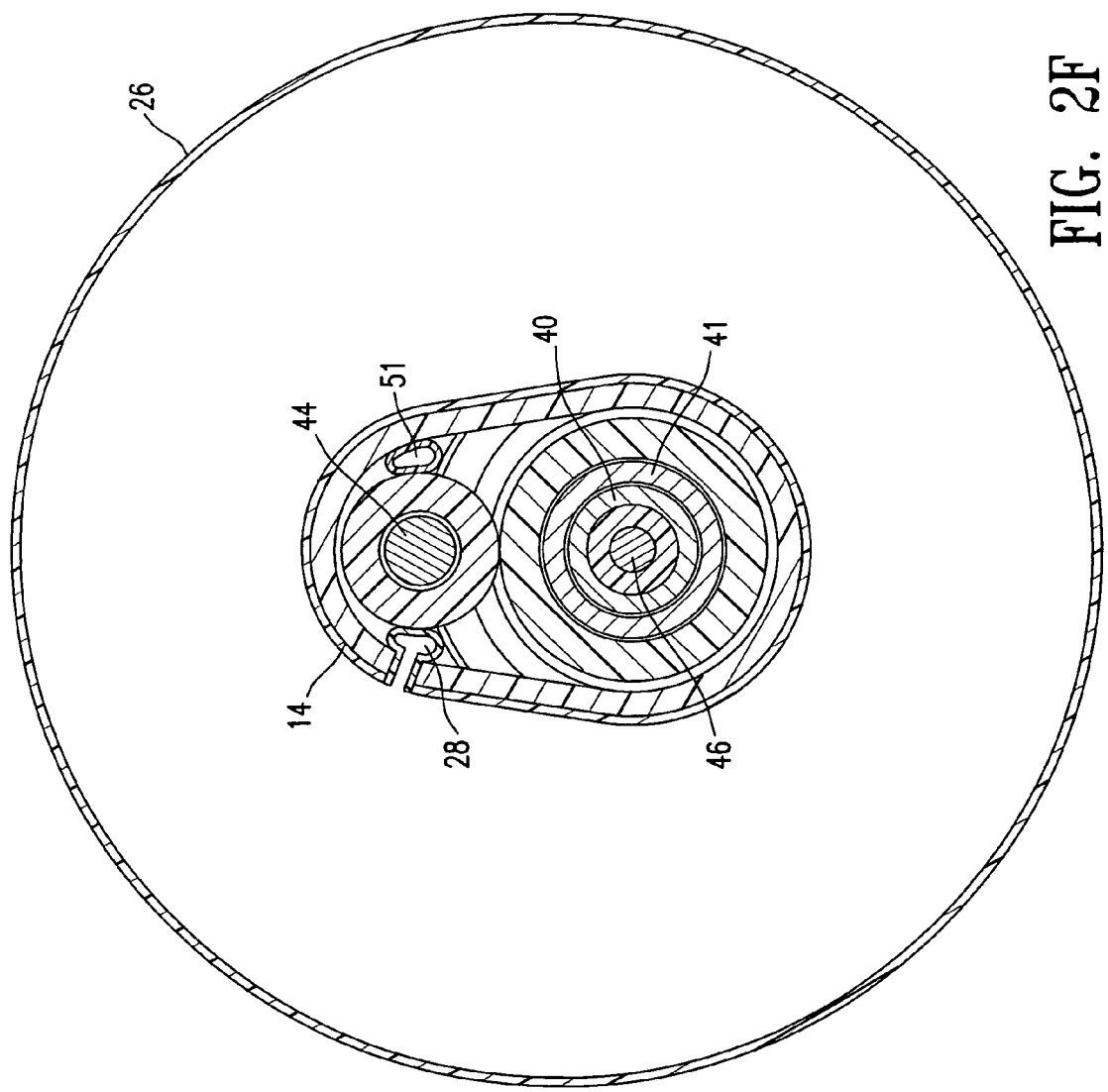

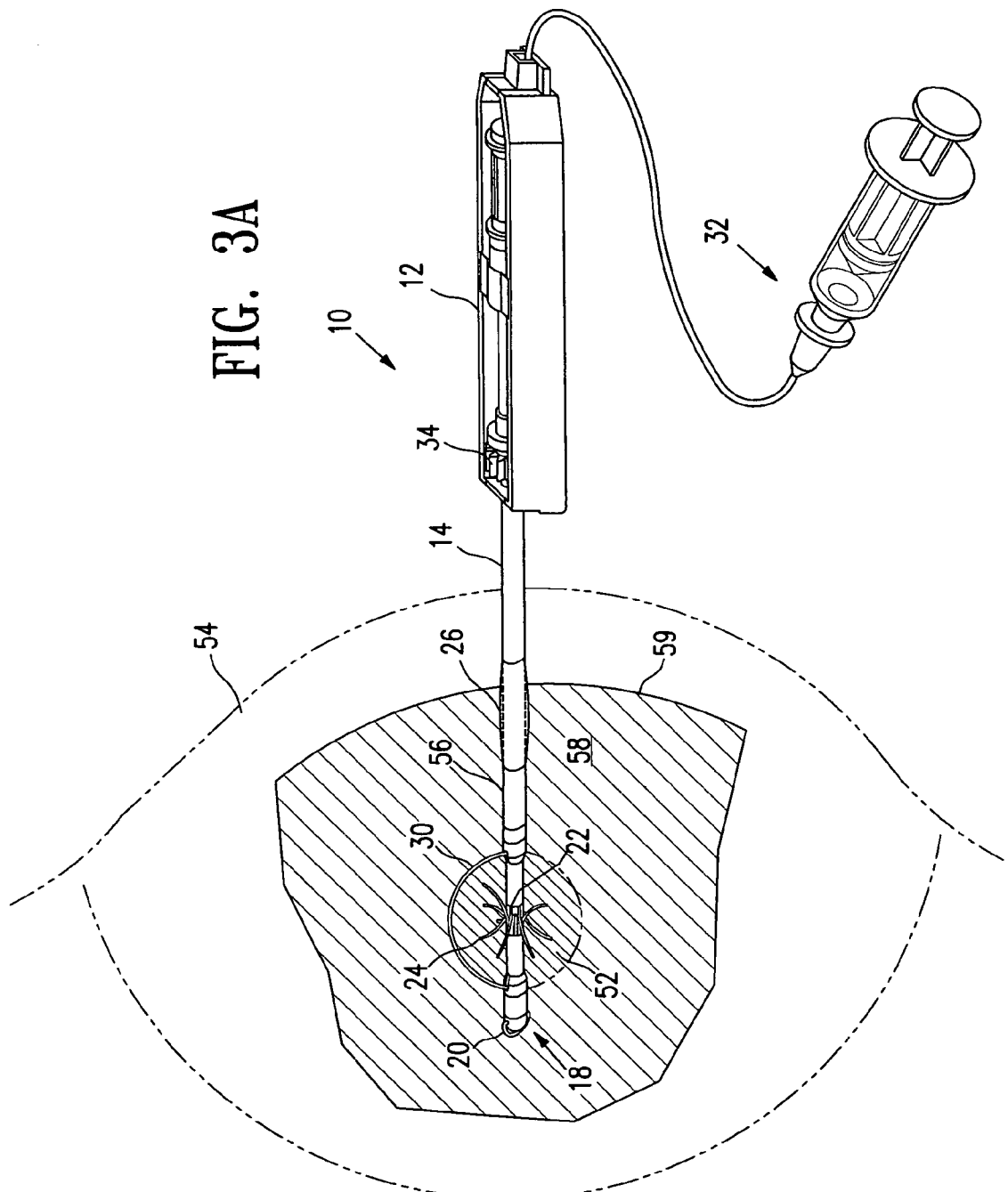

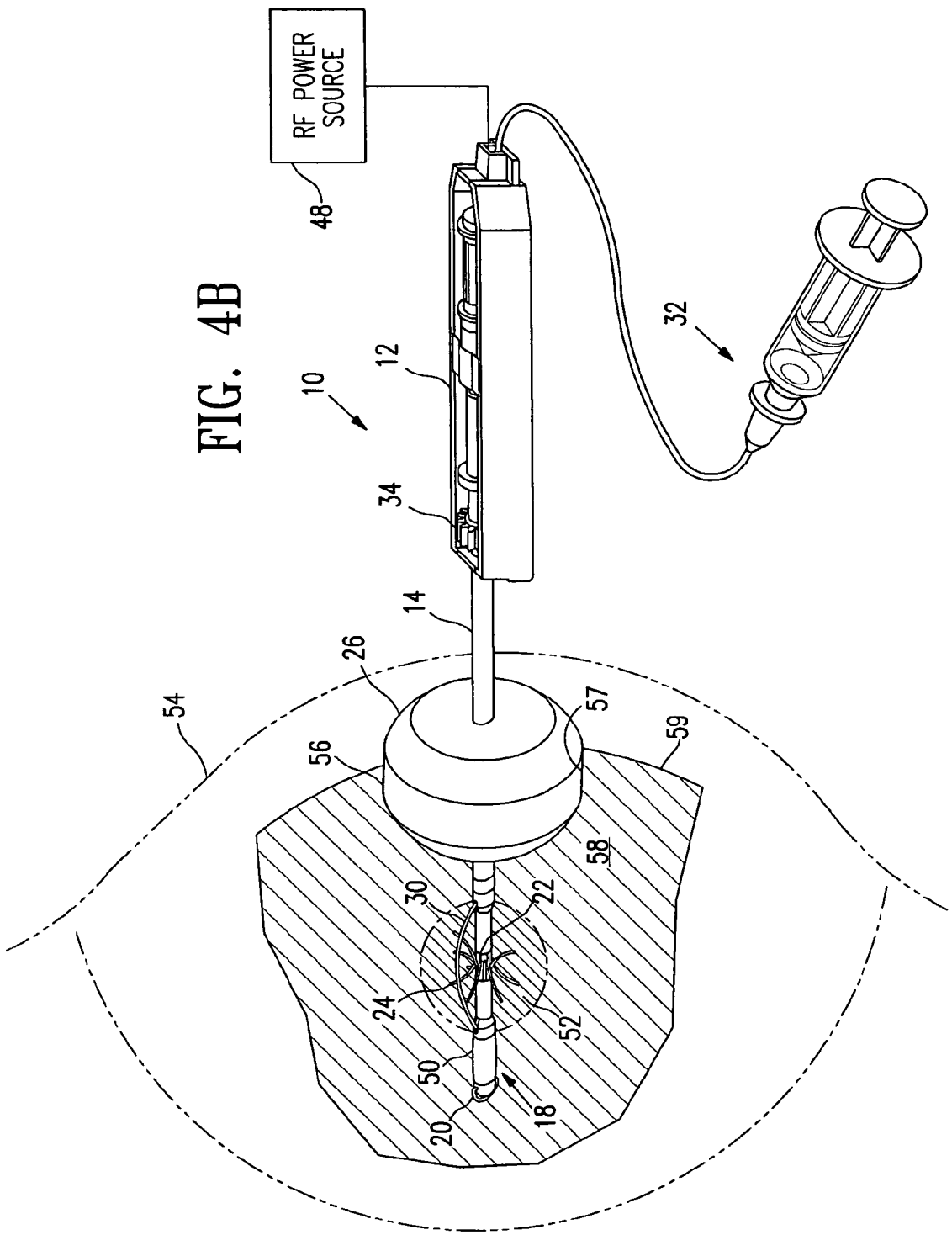

DILATION DEVICES AND METHODS FOR REMOVING TISSUE SPECIMENS

CROSS-REFERENCE TO RELATED APPLICATIONS

This application is a continuation of co-pending application Ser. No. 09/916,937, filed Jul. 27, 2001 now U.S. Pat. No. 6,997,885, which is incorporated herein in its entirety by reference and which priority is claimed.

FIELD OF INVENTION

This invention relates generally to medical devices, particularly devices for removing tissue specimens from within a patient's body, such as biopsy devices, and methods for using such devices.

BACKGROUND OF THE INVENTION

In diagnosing and treating certain medical conditions, such as potentially cancerous tumors, it is often medically desirable to remove a tissue mass. For example, during a biopsy a specimen of suspicious tissue may be removed for pathological examination and analysis, and in a lumpectomy a suspicious mass is removed from a patient's breast to preclude spread of malignant tissue. Tissue that is removed during a biopsy, lumpectomy, or other procedure may include all or part of the identified tissue mass, and may also include a surrounding margin of healthy tissue. In order to minimize bleeding, trauma to the patient, and for cosmetic reasons, the path through which the biopsy instrument passes into a patient's body is preferably a small one. However, in order to collect enough tissue to allow for a proper diagnosis, or to insure that no malignant tissue remains within a patient's body, it is often desirable to remove a mass of tissue that is wider than the entry path. In many cases removal of this large tissue mass requires further trauma to the patient, including cutting or tearing the skin and tissue of the patient in order to enlarge the exit path for removal of the tissue.

Accordingly, devices and methods for removing a tissue specimen without cutting or causing unnecessary additional trauma to the patient are desired.

SUMMARY OF THE INVENTION

This invention is directed to a tissue removing device, such as a biopsy device, and method of use thereof and, more specifically, a device for the relatively non-traumatic removal of a tissue mass through a tissue passageway leading to the tissue mass which has smaller transverse dimensions than the tissue mass.

The tissue removal device embodying features of the invention generally has an elongated shaft with a distal region for securing the tissue mass to be removed and a tissue expander proximal to the tissue securing region to expand the tissue passageway to facilitate the tissue mass removal.

The tissue expander surrounding the shaft may take a variety of forms. For example, the expander may be in the form of an inflatable balloon secured to the shaft and having an interior in fluid communication with a passageway in the elongated shaft to deliver inflation fluid to the balloon. Other forms include dilation plates which deploy radially away from a shaft, elongated members which expand arcuately away from a shaft or which expand spirally away from a shaft, and a meshwork which expands radially away from a shaft.

The invention provides devices and methods for use in removing tissue samples and suspect tissue masses from within a patient's body while minimizing trauma to the patient. The devices and methods of the invention expand and widen the entry path leading to the tissue to be removed, thereby aiding in its removal form the patient's body. Such expansion or widening of the entry path, also termed dilation, is accomplished by devices that exert outward pressure on the walls of the tissue path. In one embodiment, devices having a balloon or balloons dilate the tissue path with balloon inflation. In another embodiment, arms inserted into the path, which may have end plates or other specialized shapes configured to engage tissue, exert outward pressure on the walls of the tissue path by outward movement of the arms so that the arms and end plates press outwardly on the path to widen it.

In an embodiment, the invention provides an intracorporeal device having an elongate shaft with a cutting surface attached to a distal portion of the shaft, and an inflatable balloon attached to the elongate shaft. In embodiments of the invention, the inflatable balloon is attached to the shaft proximal of the distal end of the shaft. In further embodiments, the device has a plurality of inflatable balloons attached to the shaft. In embodiments of the invention, the plurality of balloons includes a distal balloon attached to a distal portion of the elongate shaft, and a proximal balloon attached to the elongate shaft proximal of the distal balloon.

The devices of the invention may include a cutting surface or a plurality of cutting surfaces. For example, a device embodying features of the invention may have a cutting surface attached to its distal end. A device with a plurality of cutting surfaces may have a cutting surface attached to its distal end and another cutting surface attached to the elongate shaft proximal of the distal end. Thus, intracorporeal devices having a single cutting surface or a plurality of cutting surfaces may include a balloon or a plurality of balloons, where the balloons include a distal balloon attached to a distal portion of the elongate shaft, and a proximal balloon attached proximally of the distal balloon. Devices embodying features of the invention may also include an anchoring device, which may include at least one extendable element configured to deploy from a retracted position adjacent the elongate shaft to an extended position.

In yet further embodiments, the invention provides an intracorporeal device including an elongate shaft with a plurality of cutting surfaces, including a distal cutting surface attached to the distal end and a side cutting surface extendably and retractably attached to the elongate shaft proximal of said distal end; and having a balloon or a plurality of balloons attached to the elongate shaft. The plurality of balloons may include a distal balloon attached to a distal portion of the elongate shaft, and a proximal balloon attached to the elongate shaft proximal of the distal balloon. The side cutting surface may be attached to the elongate shaft between proximal and distal balloons. The device may further have an anchoring device, which may include at least one extendable element configured to deploy from retracted position adjacent said elongate shaft to an extended position. The anchoring device may be attached to the elongated shaft between a distal balloon and a proximal balloon.

The invention also provides methods for removing a tissue specimen from a tissue bed within a patient's body with a device having a balloon or balloons. The methods include positioning a device embodying features of the invention along a path in a tissue bed within a patient's body; inflating a balloon effective to dilate the path; and removing the tissue specimen. The methods of the invention may further include anchoring the tissue specimen to said intracorporeal device.

According to the methods of the invention, a balloon, or a plurality of balloons, including, e.g., a proximal balloon and a distal balloon, may be inflated to aid in the removal of the tissue specimen. In embodiments, inflation of a proximal balloon is effective to dilate a path leading to a tissue mass within a patient's body. In other embodiments, inflation of a distal balloon is effective to aid in the removal of a tissue specimen from a tissue bed.

Devices embodying features of the invention may have means other than balloons for dilating a path leading to a tissue mass within a patient. In yet further embodiments, the invention provides a dilation device for dilating a path within a patient's body, including a proximal handle portion; a distal dilation portion having an expandable transverse dimension and at least one inner surface configured to enclose at least a portion of a shaft; and a dilation mechanism effective to enlarge the transverse dimension of the dilation portion. In embodiments, the dilation portion includes at least two arms each having distal ends with outer surfaces, the outer surfaces being configured to engage tissue. The dilation mechanism may include a pivot configured to separate the arms. In further embodiments, the handle portion may include a pair of legs operably connected to the pivot and arms effective that motion of the legs together is effective to separate the two arms.

In further embodiments, the invention provides a method for dilating a path within a patient's body, where the path contains an elongated shaft at least partly therethrough, including the steps of enclosing at least a portion of the elongated shaft with at least a distal dilation portion of a dilation device having an expandable transverse dimension, at least one inner surface configured to enclose at least a portion of an elongated shaft, and at least one outer surface configured to engage tissue; and enlarging the transverse dimension of said dilation portion effective to dilate a path through the tissue bed. The distal dilation portion may include at least two arms each having distal ends with outer surfaces, the outer surfaces being configured to engage tissue, further comprising a step of separating the at least two distal ends effective to engage tissue within said tissue bed; the methods may further include steps of compressing the handle portion effective to separate said at least two distal ends, and where the dilation mechanism includes a pivot, the compression of the handle portion is effective to rotate said at least two arms about said pivot effective to separate the arms. The handle portion may be a single handle connected to both legs of the device, or may be separate handle portions for each leg.

The devices and methods of the invention are useful for enlarging an exit path for removal of tissue samples from within a patient's body. In some embodiments, the devices include balloons, and in other embodiments, the devices include mechanical devices including a pivot. The balloon and mechanical devices and methods may be used individually, or may be used together, to provide the advantage of enabling the removal of tissue samples without need for cutting or tearing the skin, or for creating large entry wounds to remove tissue. Thus, the devices and methods of the invention minimize trauma to a patient during biopsy, lumpectomy, or other such procedures, and reduce resulting physical and cosmetic damage to the patient.

BRIEF DESCRIPTION OF THE DRAWINGS

FIG. 2F is a cross-sectional view of the device of FIG. 2C taken along line 2F-2F.

FIG. 2G is a cross-sectional view of the device of FIG. 2C taken along line 2G-2G.

FIG. 3A is a perspective view of a device embodying features of the invention having a balloon in a deflated configuration, anchored in place in a breast shown in phantom.

FIG. 4B is a perspective view of the device of FIG. 4A with the proximal balloon in an inflated configuration and dilating a path out from within a breast shown in phantom.

DETAILED DESCRIPTION OF THE INVENTION

Figure 1A:
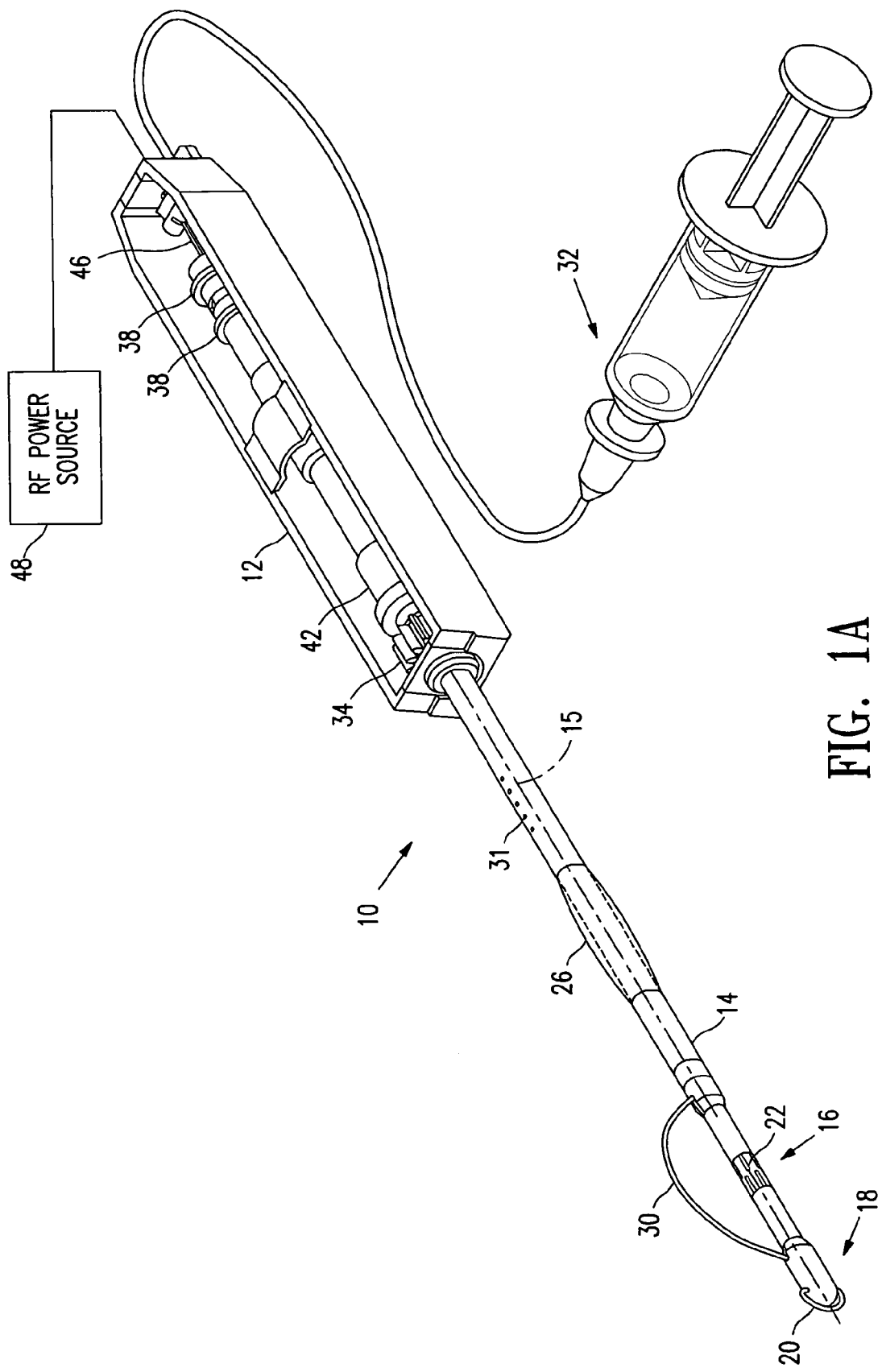
FIG. 1A is a perspective view of a device embodying features of the invention having a balloon, showing the balloon in a deflated configuration.
Figure 1B:
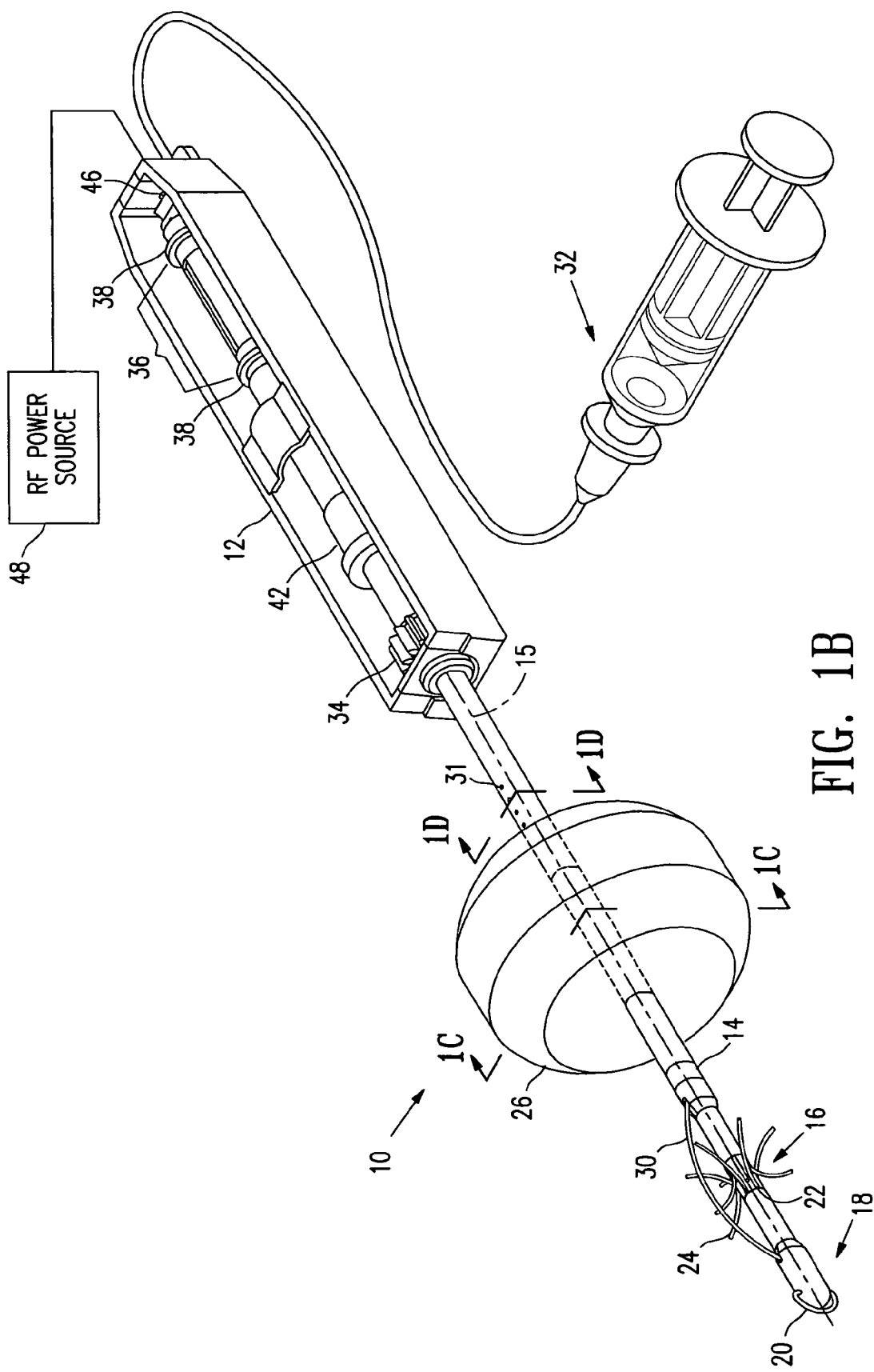
FIG. 1B is a perspective view of a device embodying features of the invention having a balloon, showing the balloon in an inflated configuration.

FIGS. 1A and 1B show a balloon dilation device 10 including a handle 12, and an elongate shaft 14 oriented along a longitudinal axis 15 defining a distal direction away from handle 12 and a proximal direction towards handle 12. The elongate shaft 14 has a distal portion 16 with a tip 18. A distal cutting surface 20 is shown in this embodiment to be an arcuate electrosurgical cutter spaced distally from tip 18. Slots 22 along shaft 14 house anchor elements 24 (retracted so not shown in FIG. 1A) shown in an extended configuration in FIG. 1B. Anchor elements 24 may extend from slots 22 to anchor the device 10 to adjacent tissue. Side cutting surface 30, shown in FIG. 1A in an extended configuration and in FIG. 1B in a retracted configuration, may be used to cut tissue to isolate a mass of tissue from a surrounding tissue bed within a patient's body. Side cutting surface 30 may be an electrosurgical cutter as illustrated in FIGS. 1A and 1B.

Device 10 illustrated in FIG. 1A and FIG. 1B has a single balloon, proximal balloon 26, located proximal of the tip 18 along shaft 14 and shown in a deflated configuration in FIG. 1A and in an inflated configuration in FIG. 1B. Proximal balloon 26 may be inflated by passage of a fluid, which may be either a gas or a liquid, along inflation tube 28 into proximal balloon 26. The fluid is caused to flow into and inflate balloon 26 by pressure from an inflation mechanism 32, illustrated in FIGS. 1A and 1B as a syringe connected to the device 10 by a tube.

FIG. 1B shows device 10 with proximal balloon 26 in an inflated configuration. Inflation of balloon 26 while device 10 is in place within a path leading to a tissue specimen within a patient's body presses balloon 26 against body tissue, effective to compress and displace the body tissue and to expand the path. Tissue specimens may be removed through the path as the device is withdrawn from the body. Fixation of the tissue mass 52 to the shaft 14 by anchor elements 24 brings the tissue mass 52 out of the tissue bed 58 as the device 10 is withdrawn from the patient's body. The expanded path makes possible the removal of larger tissue specimens than would otherwise be possible, and eases the removal of all tissue specimens regardless of size while minimizing trauma and damage to the patient.

Figure 1C:
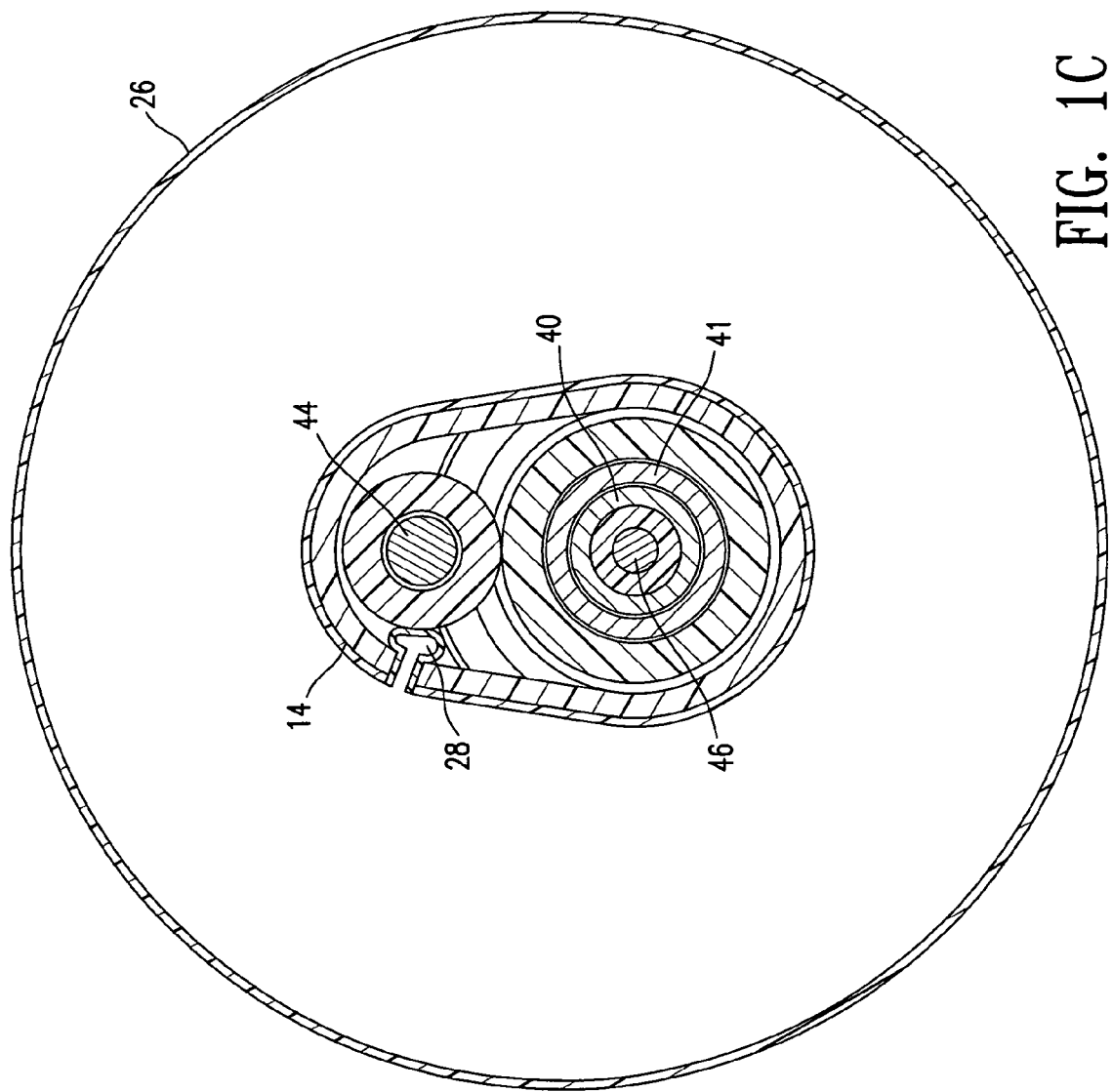
FIG. 1C is a cross-sectional view of the device of FIG. 1B taken along line 1C-1C.
Figure 1D:
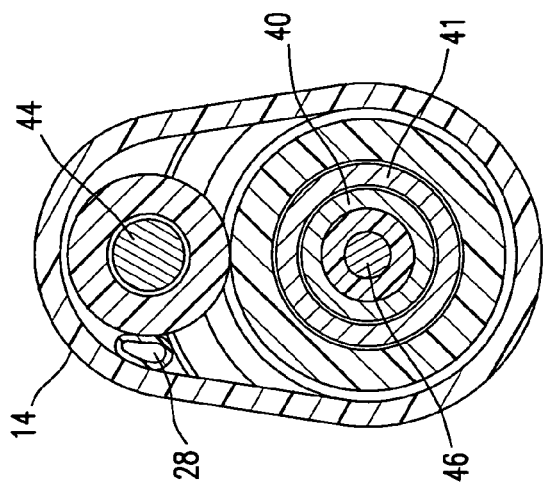
FIG. 1D is a cross-sectional view of the device of FIG. 1B taken along line 1D-1D.

Side cutting surface 30 may be extended and retracted by movement of side-cutter deployment shaft 44 effected by side-cutter shuttle 42. Handle 12 includes within it rotary mechanism 34 effective to rotate shaft 14, and anchor element extension mechanism 36 for extending anchor elements 24 into tissue, comprising shuttles 38 visible in the view shown in FIGS. 1A and 1B. Shuttles 38 connect with deployment shafts 40 and 41 shown in FIGS. 1C and 1D. Conductor 46 provides electrical power to distal cutting surface 20 by connecting power source 48 with distal cutting surface 20. Power source 48 may be a source of radiofrequency (RF) power.

Distal cutting surface 20 is effective to cut tissue and so to aid in the entry of device 10 into, and the passage through, a patient's body. In preferred embodiments, distal cutting surface 20 and side cutting surface 30 are electrosurgical cutting elements receiving RF power from power source 48 effective to cut tissue. In addition, cutting surfaces 20 and 30 may be used to cauterize tissue when desired. Rotation of shaft 14 while side cutting element 30 is in a deployed configuration is effective to cut a path through surrounding tissue and to isolate a tissue specimen around the shaft 14 of device 10.

In embodiments of the invention, the device 10 may have a plurality of balloons. As illustrated in FIGS. 2A-2G, a device 10 embodying features of the invention has two balloons, a proximal balloon 26 and a distal balloon 50. Both balloons 26 and 50 are shown in a deflated configuration in FIG. 2A; proximal balloon 26 is shown inflated, and distal balloon 50 deflated, in FIG. 2B; and both balloons 26 and 50 are shown inflated configurations in FIG. 2C. Fluid may flow into balloons for inflation. Fluid flows into proximal balloon 26 via tube 28 and into distal balloon 50 via tube 51.

Figure 2A:
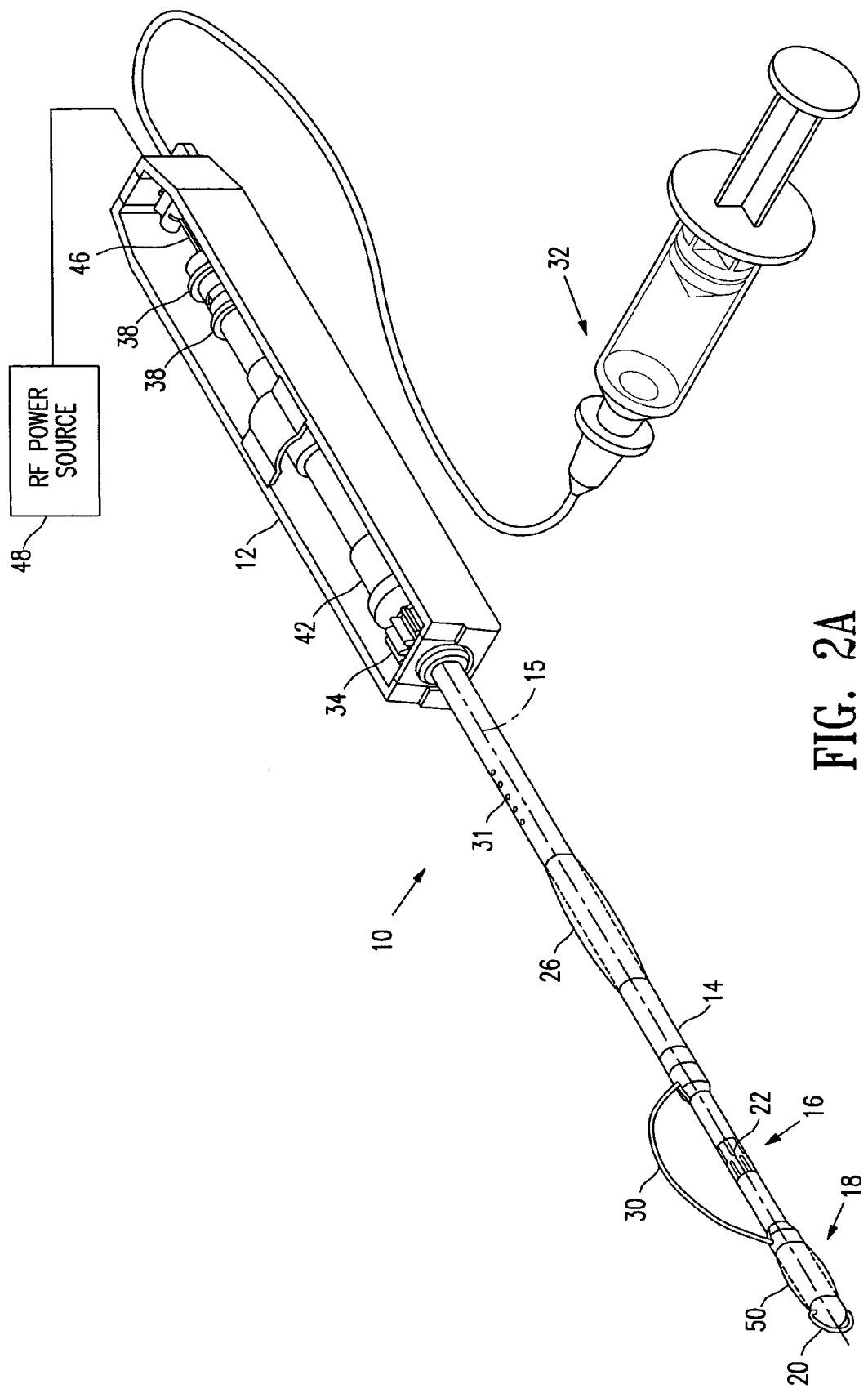
FIG. 2A is a perspective view of a device embodying features of the invention having two balloons, showing the balloons in a deflated configuration.
Figure 2B:
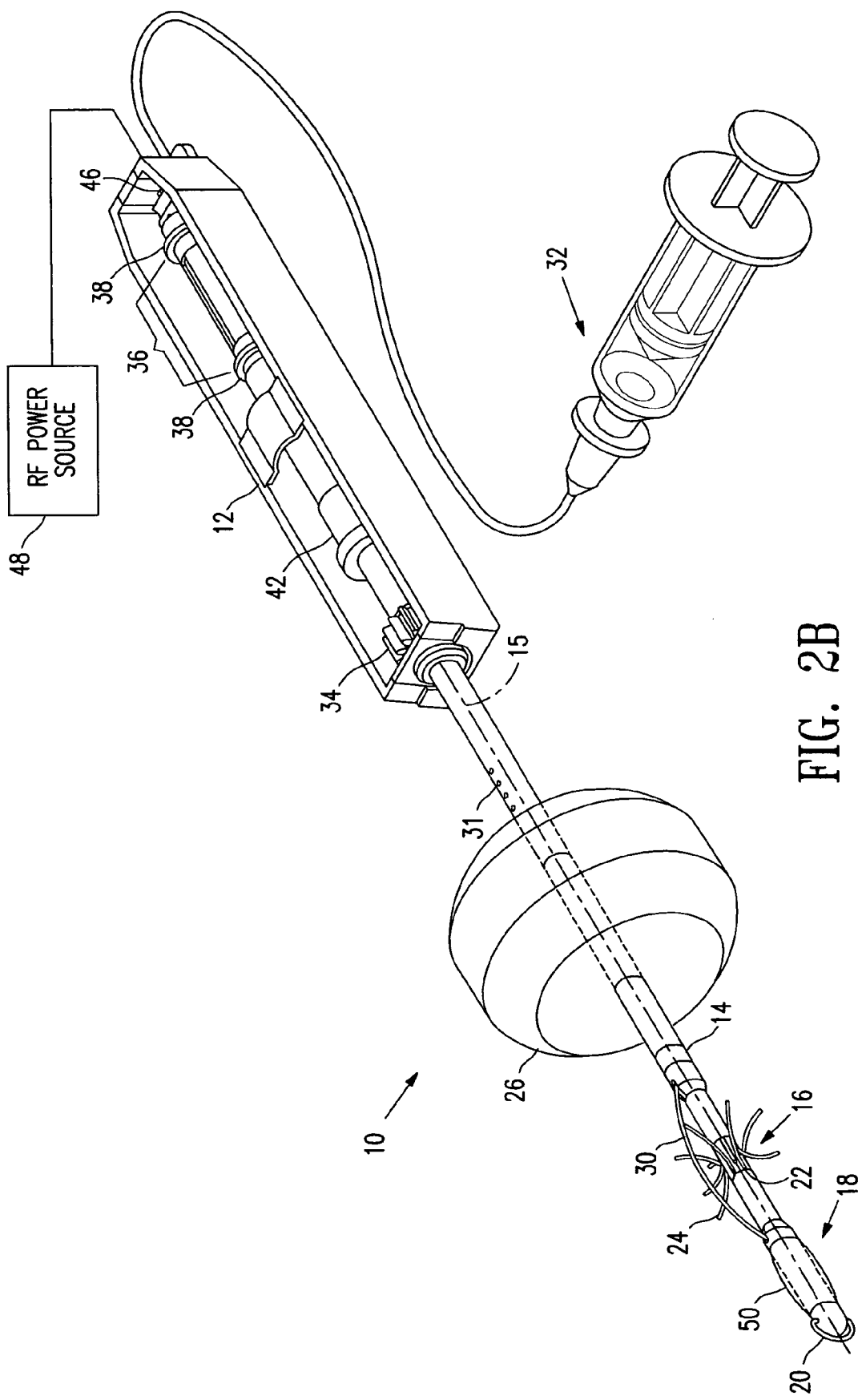
FIG. 2B is a perspective view of a device embodying features of the invention having two balloons, showing the proximal balloon in an inflated configuration and the distal balloon in a deflated configuration.
Figure 2C:
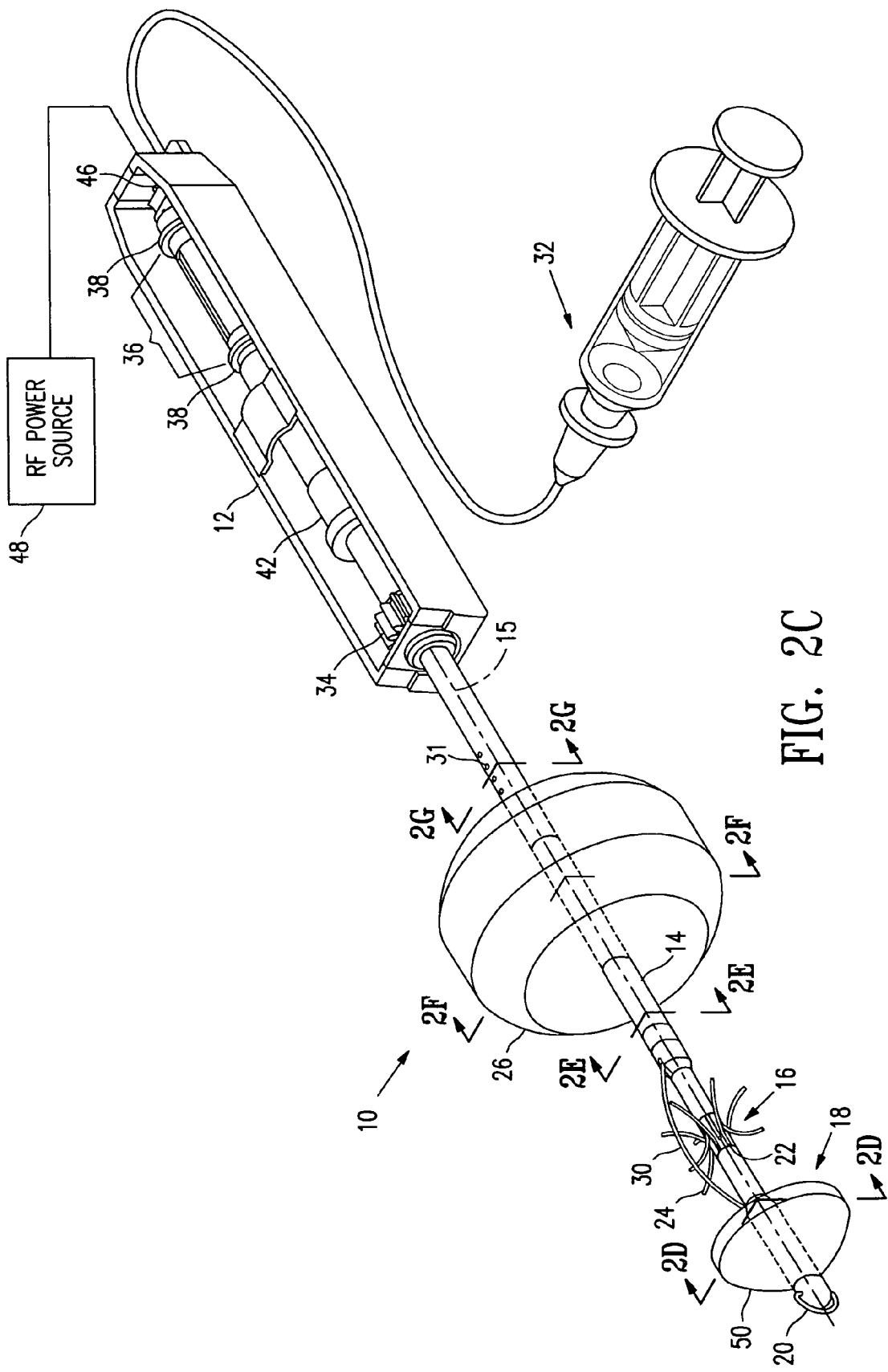
FIG. 2C is a perspective view of a device embodying features of the invention having two balloons, showing the balloons in inflated configurations.
Figure 2E:
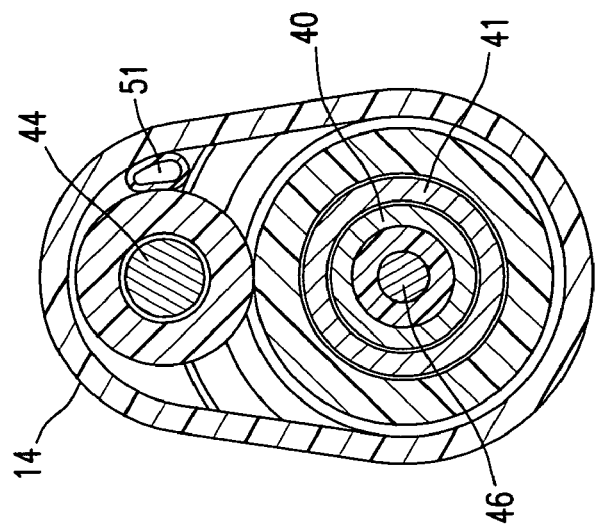
FIG. 2E is a cross-sectional view of the device of FIG. 2C taken along line 2E-2E.
Figure 2D:
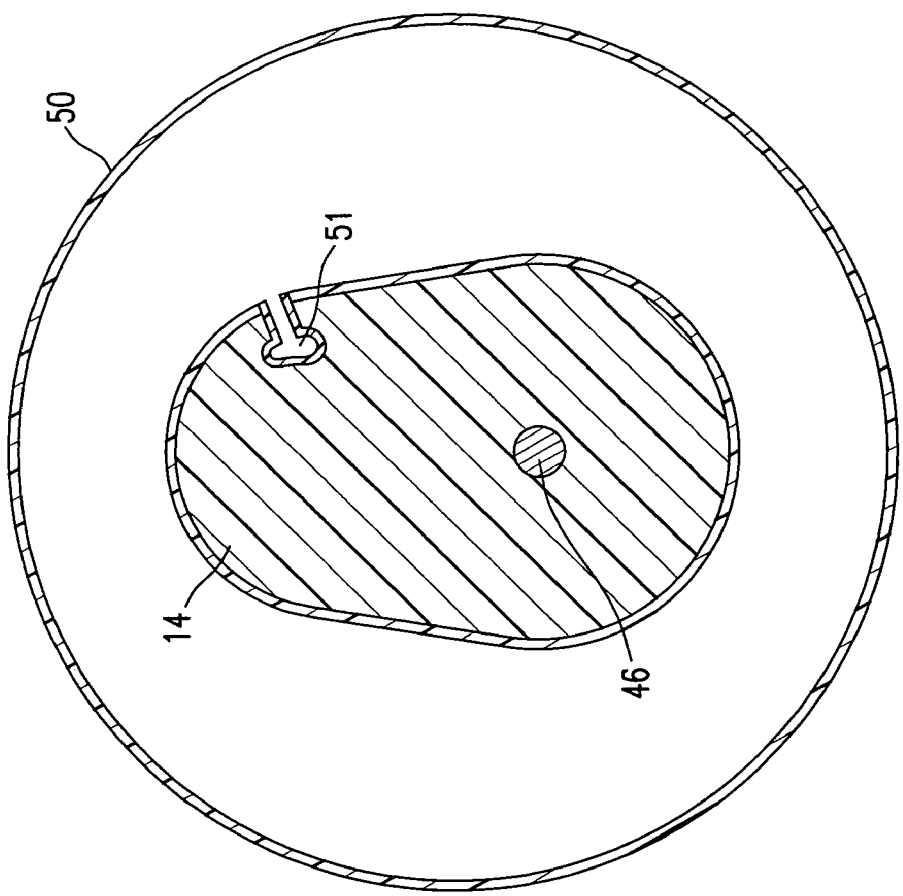
FIG. 2D is a cross-sectional view of the device of FIG. 2C taken along line 2D-2D.

The device 10 having two balloons 26 and 50 is shown in cross section in FIGS. 2D-2G. FIG. 2D is a cross-sectional view of the device of FIG. 2C taken along line 2D-2D, and shows the outer circumference of distal balloon 50 and elements of shaft 14, including anchor elements 24, anchor element deployment shaft 40, and distal cutting surface conductor 46. FIG. 2E is a cross-sectional view of the device of FIG. 2C taken along line 2E-2E, showing side cutting surface 30 and the region of shaft 14 between balloons 26 and 50. FIG. 2F is a cross-sectional view taken along line 2F-2F showing the outer circumference of proximal balloon 26 and shaft 14 and elements in the interior of shaft 14. A cross-sectional view of the device 10 proximal of balloon 26, taken along line 2G-2G, is shown in FIG. 2G. Proximal balloon inflation tube 28 and distal balloon inflation tube 51 are effective to carry fluid for inflation of proximal balloon 26 and distal balloon 50, respectively. Outflow of fluid is effective to allow balloons to deflate.

Figure 3B:
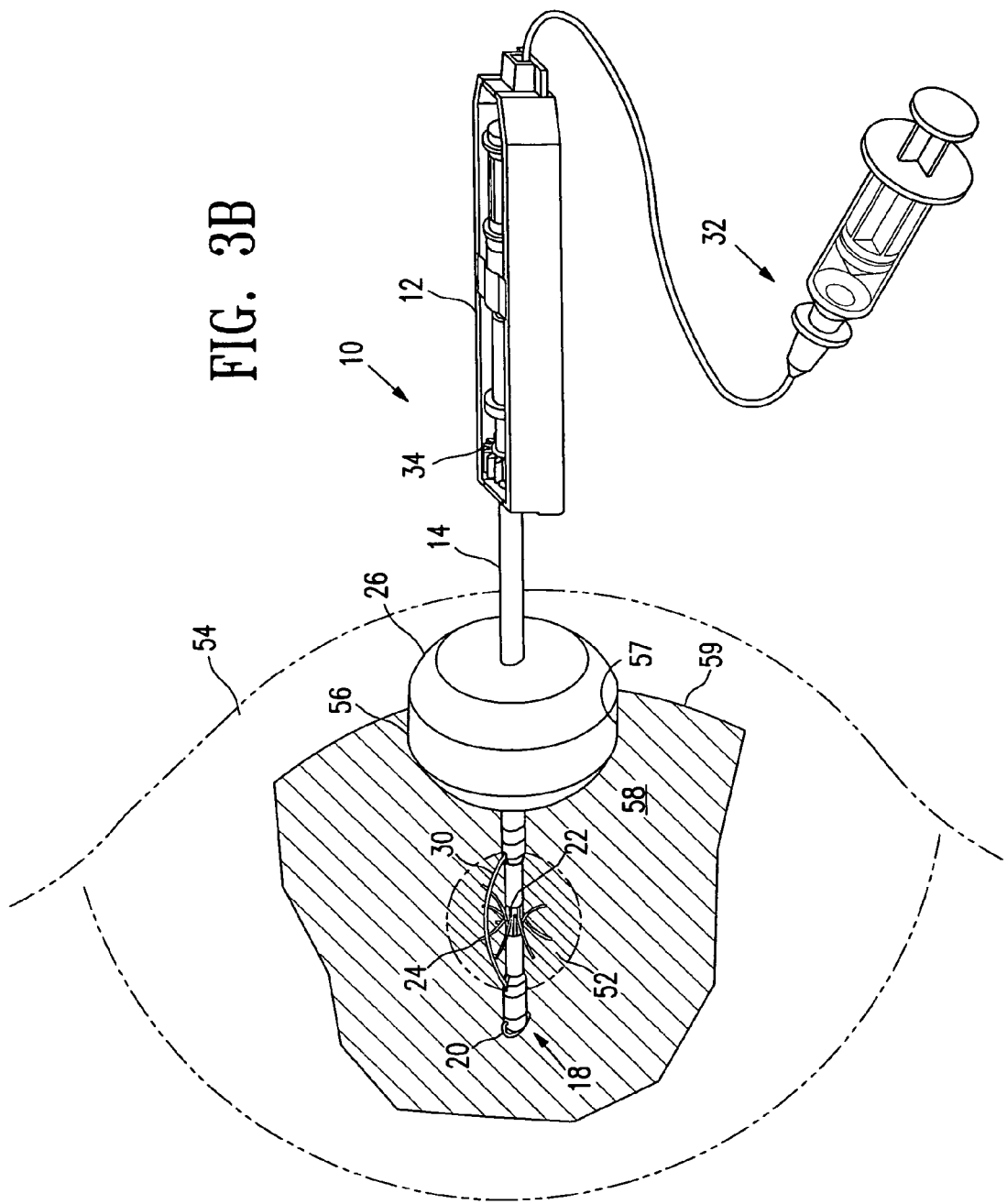
FIG. 3B is a perspective view of the device of FIG. 3A with a balloon in an inflated configuration, during removal of a tissue specimen from within a breast shown in phantom.

Devices and methods of the invention may be used to remove tissue specimens from any suitable location within a patient's body. FIGS. 3A and 3B illustrate the removal of a tissue mass 52 from within the breast 54 of a patient. A device 10 having a single balloon, proximal balloon 26, is shown in place in a breast 54 in FIGS. 3A and 3B. Anchor elements 24 are shown anchoring the isolated tissue mass 52 to the device 10. Proximal balloon 26 is in the deflated configuration in FIG. 3A, and in an inflated configuration in FIG. 3B. Inflation of proximal balloon 26 presses walls 57 of path 56 outwardly, dilating the path so it can accommodate the passage of tissue mass 52. Path 56 crosses tissue bed 58 and skin 59 and dilation of path 56 is effective to compress and stretch tissue bed 58 and skin 59 but does not tear or cause undue trauma to these parts of the patient's body. The dilation of path 56 reduces or eliminates the need for cutting tissue bed 58 or skin 59 to remove the tissue mass 52. Removal of the tissue mass 52 anchored to the shaft 14 by anchor elements 24 is accomplished by proximal movement of the device 10.

In FIGS. 3A and 3B, the elongate shaft 14 of device 10 is shown inserted into the patient with tip 18 having passed through the suspect tissue mass 52 location within a patient's body and with shaft 14 occupying a position within a path 56 through tissue bed 58, the path 56 leading to the tissue mass 52 that is to be removed. Distal cutting surface 20 is used to aid in making a path to the desired location within a patient's body and in positioning the device in a desired location. Deployment of side cutting surface 30 and rotation of shaft 14 rotated causes side cutting surface 30 to cut tissue effective to isolate a tissue mass 52 from the surrounding tissue bed 58. Distal cutting surface 20 and side cutting surface 30 may be provided with, e.g., RF power, and used as electrosurgical cutting elements. Anchoring elements 24 are shown deployed from slots 20 to anchor the isolated tissue mass 52 to the device 10. Proximal balloon 26 is shown in its inflated configuration in FIG. 3B, effective to press on tissue and expand the diameter of the path 56 leading to the isolated tissue mass 52. The expanded path more easily accommodates the removal of the isolated tissue mass 52 from within the breast 54.

Figure 4A:
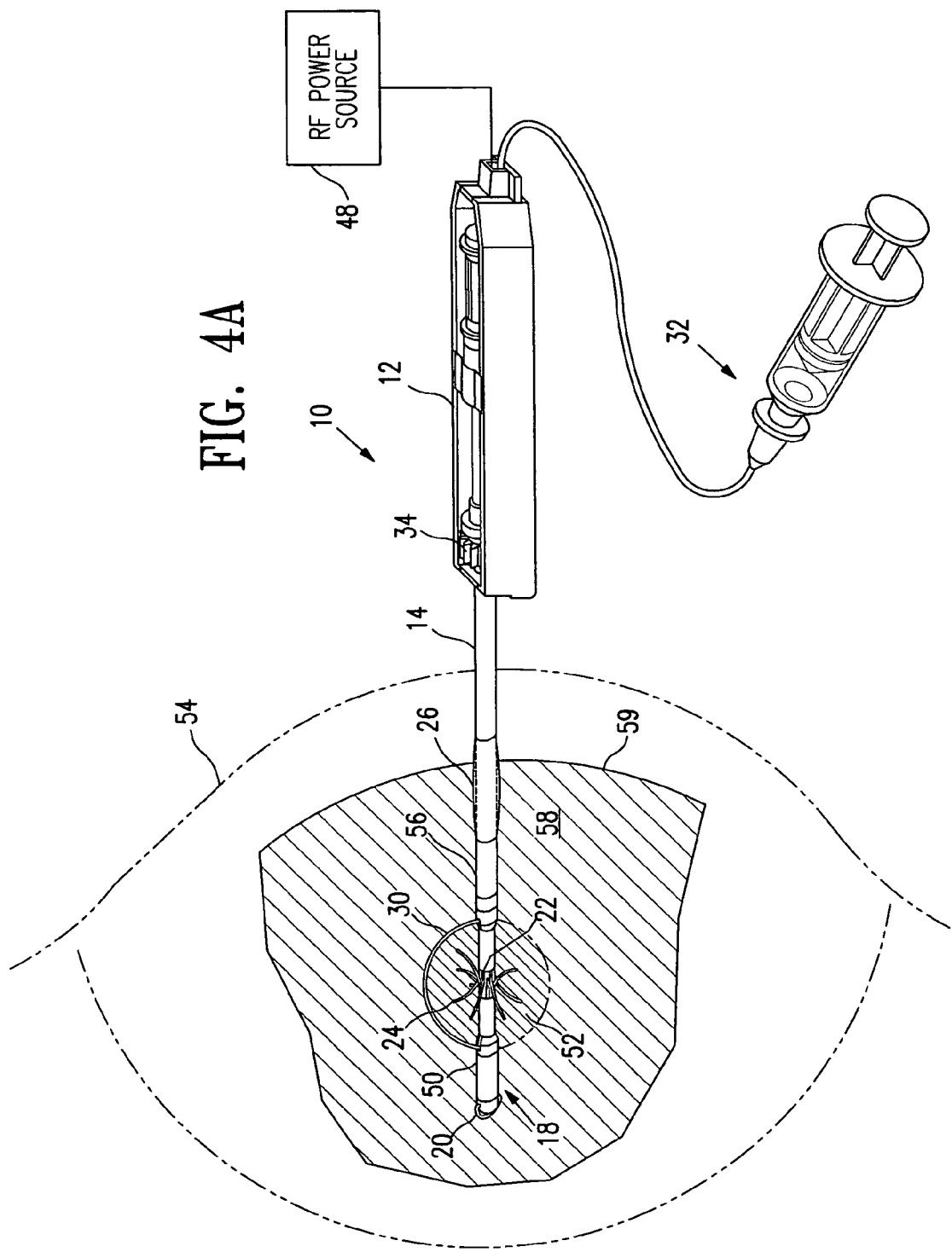
FIG. 4A is a perspective view of a device embodying features of the invention having two balloons, shown in a deflated configuration, anchored in place in a breast shown in phantom.
Figure 4C:
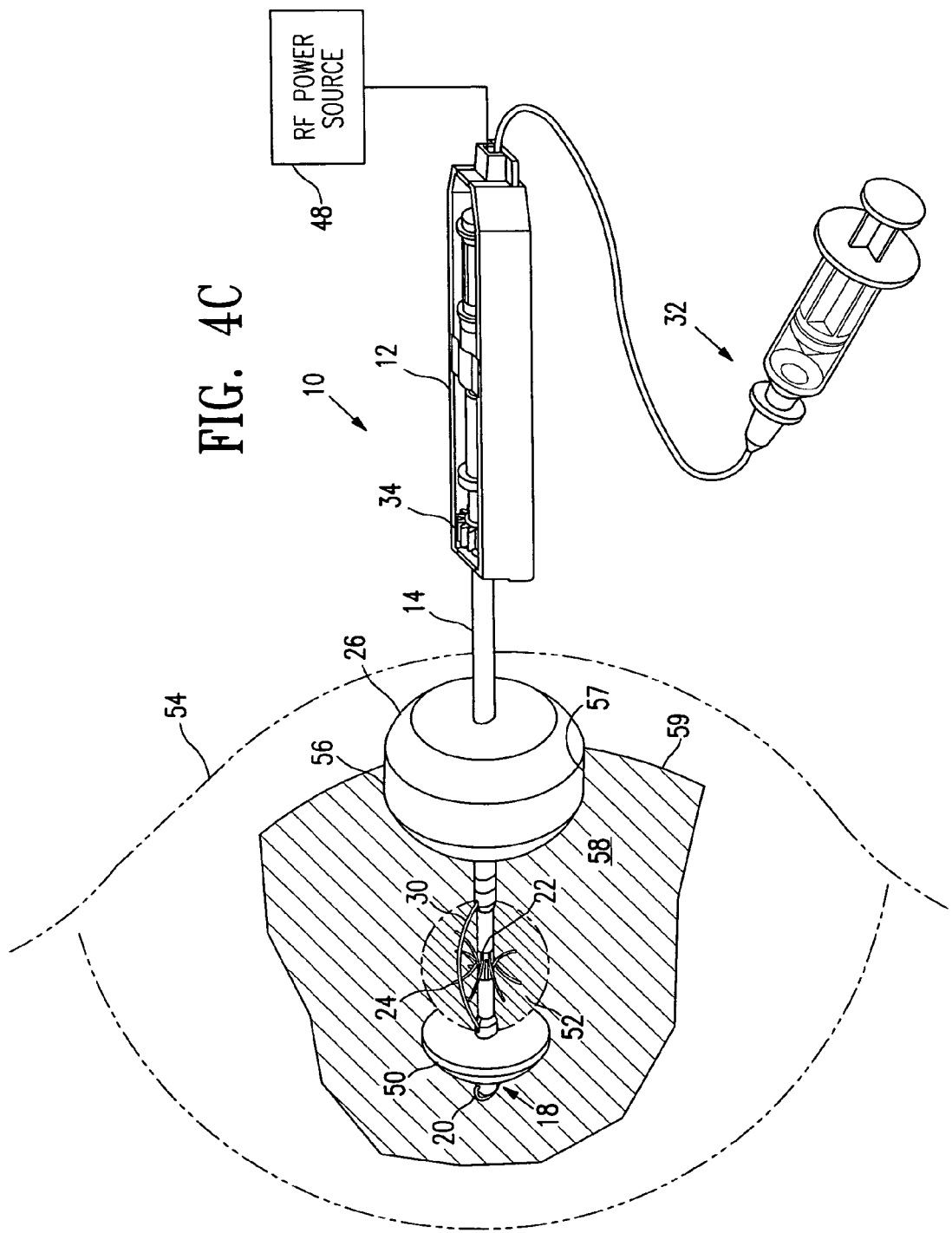
FIG. 4C is a perspective view of the device of FIG. 4A with both balloons in inflated configurations during removal of a tissue specimen from within a breast shown in phantom.

FIGS. 4A, 4B and 4C illustrate a device 10 having two balloons anchored in place in a breast 54 shown in phantom, showing the balloons deflated (FIG. 4A), the proximal balloon inflated and the distal balloon deflated (FIG. 4B), and both proximal and distal balloons inflated (FIG. 4C). In FIG. 4A, the shaft 14 is shown in place within path 56 extending through the isolated tissue mass 52, which is anchored to the shaft 14 by anchoring elements 24. FIG. 4B illustrates the device 10 of FIG. 4A with the inflated proximal balloon 26 shown dilating path 56 to aid the removal of isolated tissue mass 52. FIG. 4C illustrates the device of FIG. 4A with both balloons in the inflated configuration during removal of a tissue specimen from within a breast shown in phantom.

FIGS. 4A-4C illustrate one method of use of a device 10 having two balloons 26 and 50. In use during a diagnostic or therapeutic procedure to remove tissue from a patient, the sequence of inflation of balloons 26 and 50 would follow the sequence shown in FIGS. 2A, 2B and 2C. Thus, the elongate shaft 14 of device 10 would be inserted into the patient to bring tip 18 near to or through the desired location within a patient's body, with shaft 14 occupying a position within a path leading to the tissue mass that is to be removed. Distal cutting surface 20 may be used to aid in making a path to the desired location within a patient's body and in positioning the device in a desired location. Side cutting surface 30 may be deployed and shaft 14 rotated, thereby rotating the other elements of the device, including side cutting surface 30, and causing side cutting surface 30 to cut tissue and to isolate a tissue mass from the surrounding tissue bed. Anchoring elements 24 may be deployed from slots 20 to anchor device 10 to the isolated tissue mass 52. Proximal balloon 26 is next inflated, pressing on tissue and expanding the diameter of the path 56. The expanded path 56 may more easily accommodate the removal of the isolated tissue mass 52. Distal balloon 50 is next inflated, pressing on tissue and urging the device and attached tissue mass out along the path 56, further aiding in the removal of the isolated tissue mass 52. In preferred embodiments, and as illustrated in FIGS. 2A-2G, tip-cutting surface 20 and side cutting surface 30 may be provided with electrical power, such as RF power, and used as electrosurgical cutting elements.

Figure 5A:
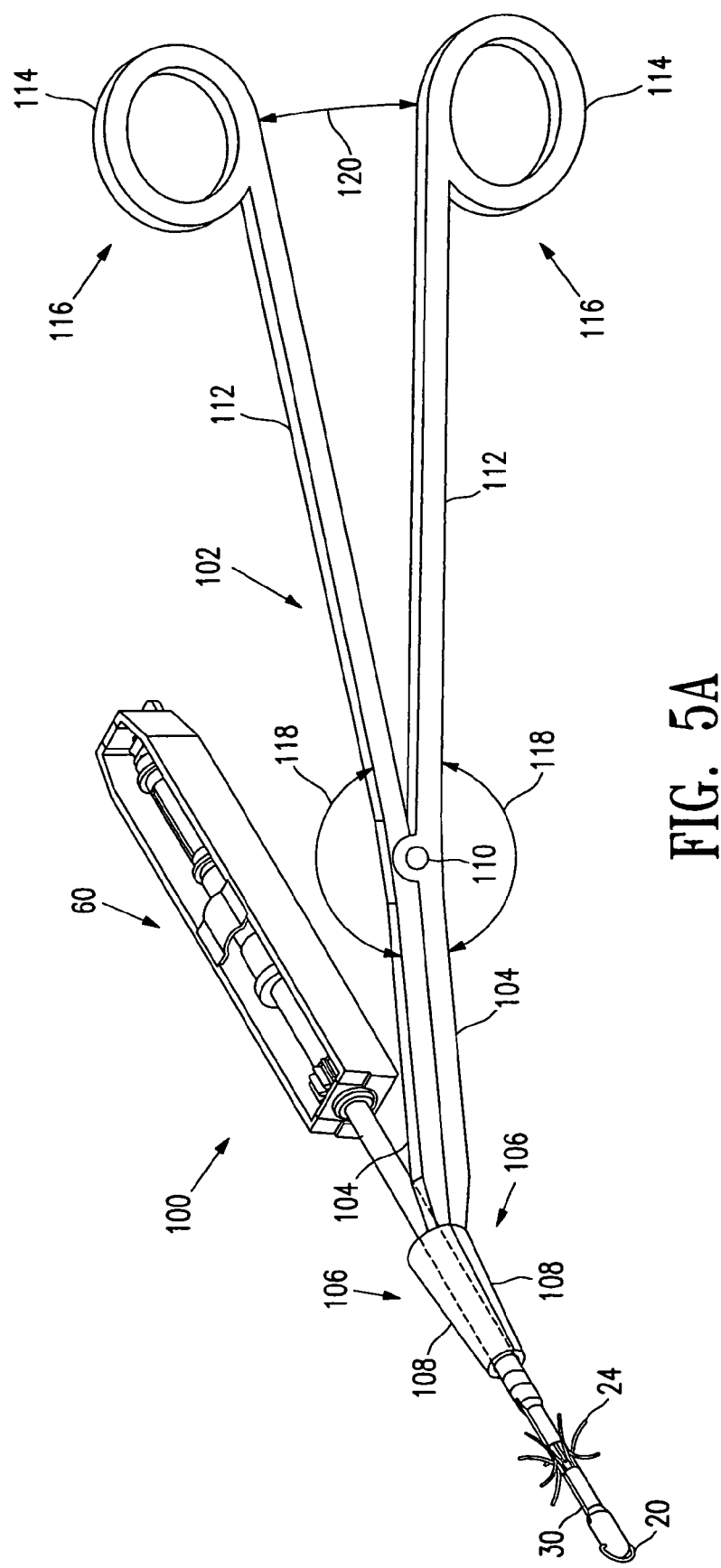
FIG. 5A is a perspective view of a mechanical dilating device embodying features of the invention showing the device in a closed configuration partially enclosing the shaft of a tissue-cutting device.

The devices of the invention may also be dilation devices having pivots, with and without inflatable balloons. Examples of dilation devices 102 without balloons are shown in FIGS. 5 and 6. Such mechanical devices 102 may be used together with balloon dilation devices 10 to form a tissue removal system 100. In addition, a tissue removal system 100 may include a tissue cutting device 60 and a dilation device 102. FIG. 5A is a perspective view of a dilation device 102 embodying features of the invention showing the device in a closed configuration partially enclosing the shaft of a tissue-cutting device 60. The tissue cutting devices shown in FIGS. 5 and 6 have features described in co-pending application Ser. Nos. 09/057,303; 09/146,185; 09/159,467; 09/238,965; and 09/356,187 named and incorporated supra. Thus, the tissue cutting devices 60 illustrated in FIGS. 5 and 6 are effective to isolate a tissue mass 52 and to anchor the mass to the device 60.

Figure 5B:
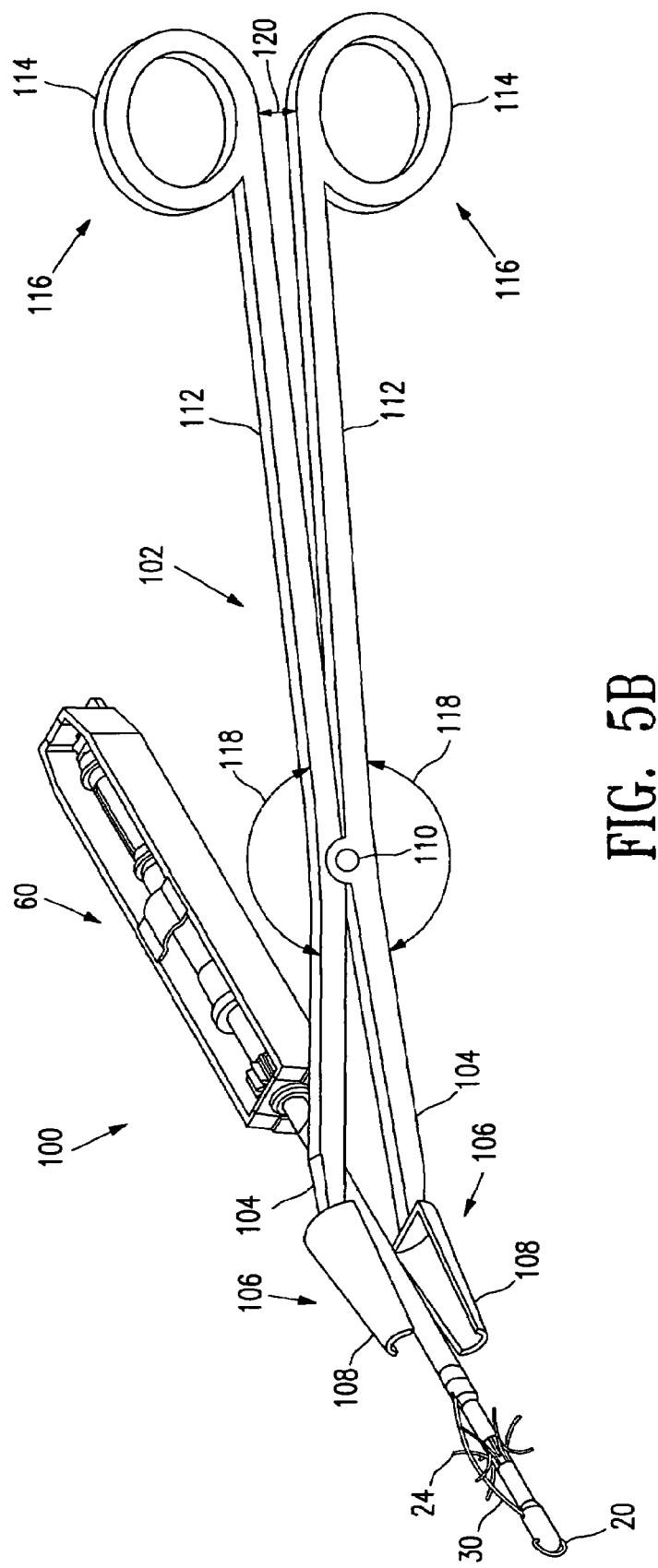
FIG. 5B is a perspective view of a mechanical dilating device embodying features of the invention shown in an opened configuration around the shaft of a tissue-cutting device.
Figure 6A:
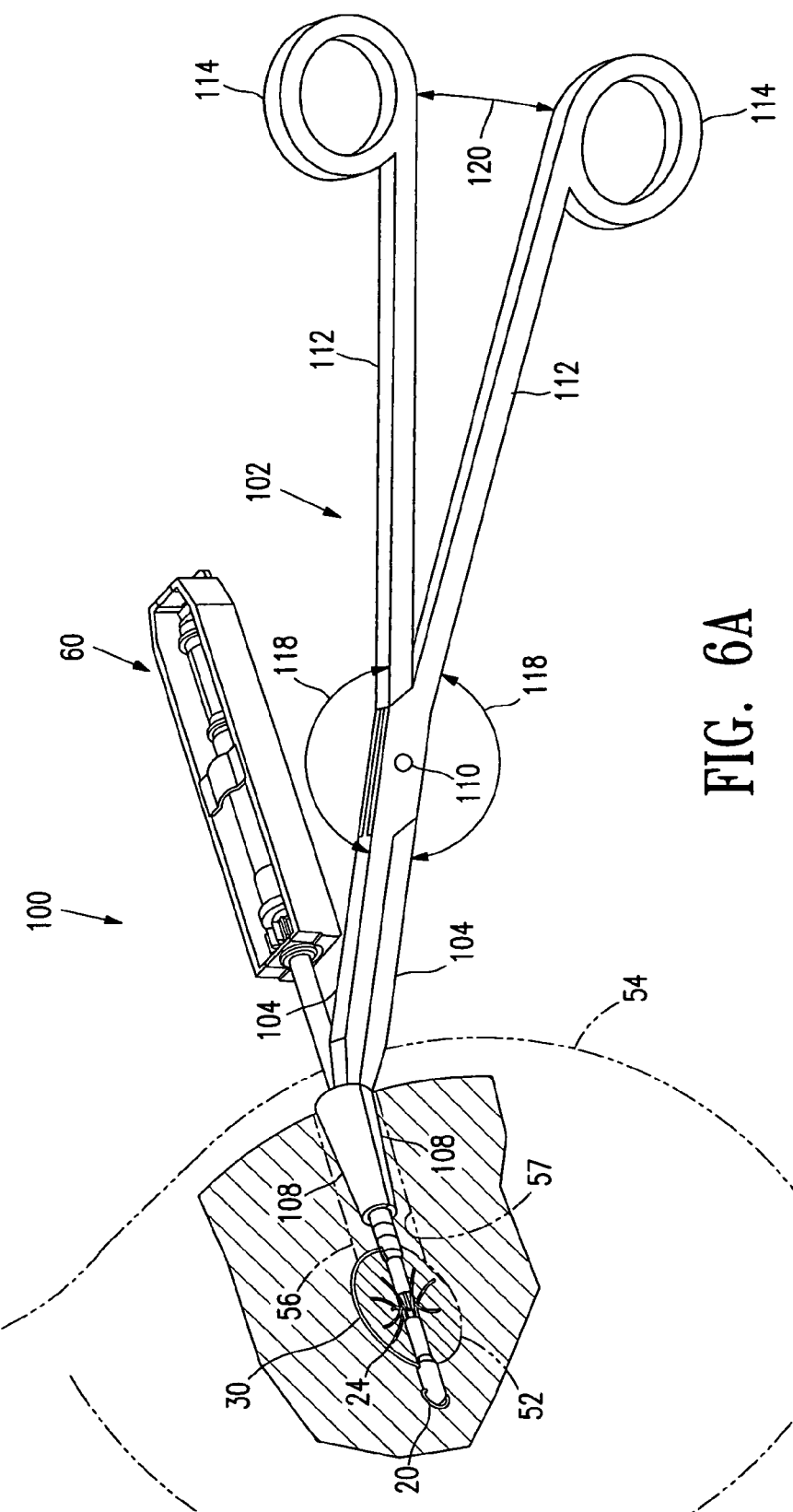
FIG. 6A is a perspective view of a mechanical device embodying features of the invention shown in a closed configuration shown in place around a tissue-cutting device in a breast shown in phantom.
Figure 6B:
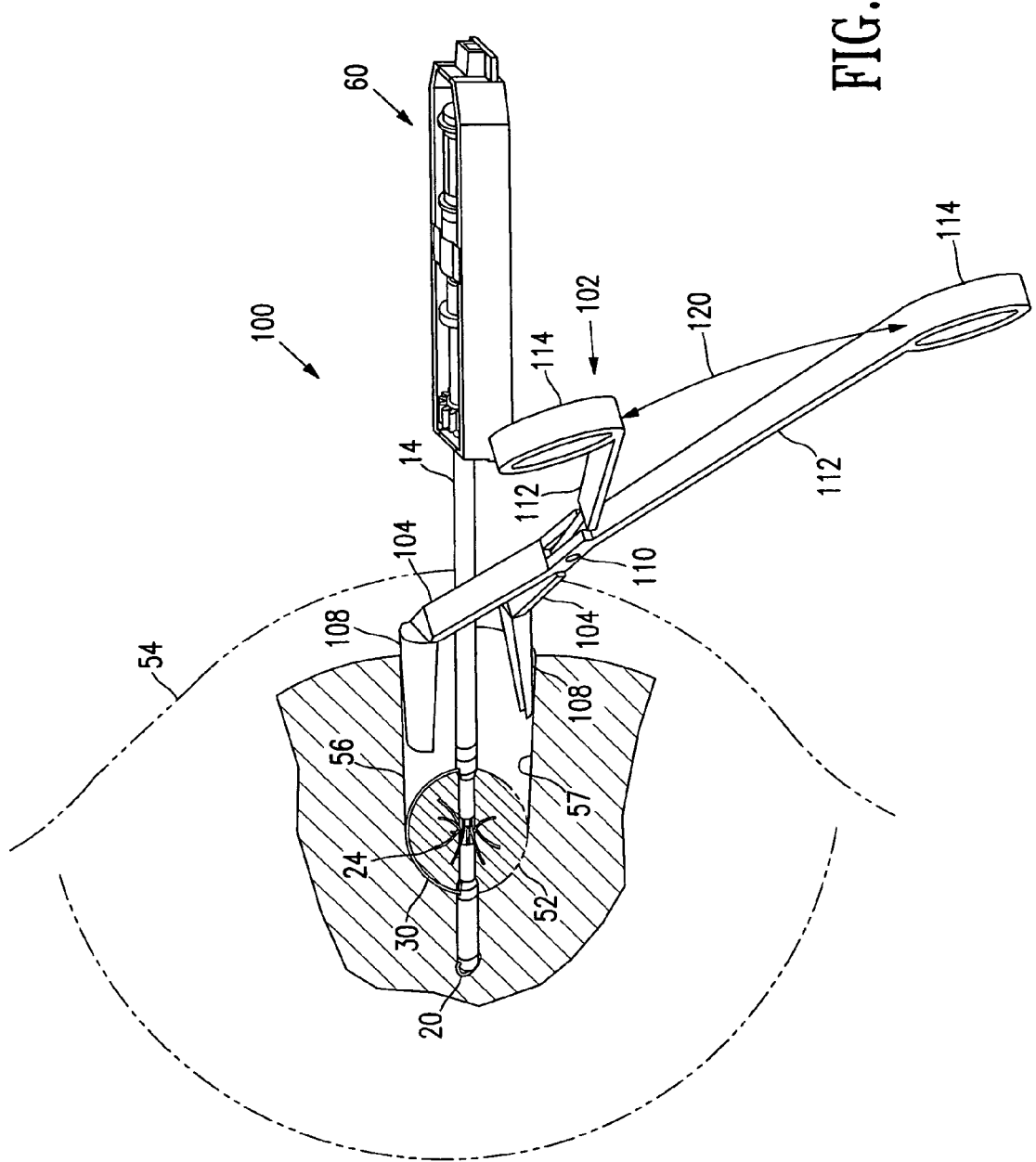
FIG. 6B is a perspective view of the device of FIG. 6A with shown in an open configuration, during removal of a tissue specimen from within a breast shown in phantom.

As shown in the tissue removal system 100 illustrated in FIGS. 5A and 5B, a dilation device 102 having features of the invention includes a pair of arm portions 104 having distal ends 106 configured to dilate tissue. As illustrated in FIGS. 5 and 6, distal ends 106 have dilation plates 108 for engaging and dilating tissue along a path within a patient's body. A pivot 110 joins the two arm portions 104 and joins leg portions 112 effective that lateral motion of leg portions 112 moves arm portions 104. As shown in FIGS. 5A, 5B, 6A, and 6B, leg and arm portions are continuous and shaped from a single piece of material, hinged by pivot 110. However, in embodiments of the invention, arm portions 104 and leg portions 112 may be formed of different pieces of material and joined together during manufacture of a dilating device 102. Leg portions 112 have handles 114 at their distal ends 116. The distance 120 between leg portions 112 is a variable distance depending on the position of leg portions 112 with respect to pivot 110. In embodiments, a single handle 114 may join legs 112.

In FIG. 5A, leg portions 110 form an angle 118 with arm portions 104 effective that movement of leg portions 110 towards each other (so as to reduce distance 120) causes arm portions 104 to separate. The result of such movement reducing the distance 120 is shown in FIG. 5B, showing arms 104 separated. Such separation of arms 104, when dilation plates 108 are in place within a path 56 within a patient's body, is effective to dilate a path 56 and to aid in the removal of a tissue specimen.

In a scissors, a blade portion is aligned with an axis parallel to a handle axis so that motion around a central pivot causes congruent motion of the blade and handle. Thus, in a scissors, separating the handles separates the blades. Such movement, where two blades are separated when two handle portions are open, is termed "scissor-like." Alternatively, where a scissors has blades and handles that are not aligned, but meet at an angle so that the handle portions are separated when the blade portions are together, squeezing the handle portion separates the blades. Such an arrangement is not scissor-like.

The configuration of arm portions 104 and leg portions 112 around pivot 110 in the device illustrated in FIGS. 5A and 5B, where arms 104 are analogous to the blades of a scissors, is not scissor-like. Connected arm portions 104 and leg portions 112 form an obtuse angle 118 around pivot 110, so that when arm portions 104 are in contact, leg portions 112 are separated, and conversely, when leg portions 112 are close together or in contact, arm portions 104 are separated. An operator holding the leg portions 112 of a dilation device 102 as illustrated in FIGS. 5A and 5B can dilate tissue in contact with dilation plates 108 by squeezing together legs portions 112. Distance 120 is larger in FIG. 5A than in FIG. 5B, the leg portions 112 shown in FIG. 5A are shown farther apart than in FIG. 5B.

FIG. 6A shows a tissue removal system 100 including a dilation device 102 shown with dilation plates 108 in a closed configuration in place around a tissue-cutting device 60 within a breast. In this embodiment, the handles 114 and arms 104 are in a scissor-like configuration. Anchor elements 24 are shown anchoring tissue cutting device 60 to an isolated tissue mass 52. Dilation plates 108 are in place within path 56 leading to isolated tissue mass 52. The mechanical dilation device 102 illustrated in FIGS. 6A and 6B differs from the dilation device 102 illustrated in FIGS. 5A and 5B in the orientation of arm portions 104, pivot 110 and leg portions 112, the devices having different angles 118 and behaving differently in response to reduction in distance 120 between leg portions 112. Reduction in distance 120 effects separation of arm portions 104 in the device 102 illustrated in FIGS. 5A and 5B. However, the dilation device 102 illustrated in FIGS. 6A and 6B is configured so that increasing distance 120 between leg portions 112 is effective to separate arm portions 104 and to press dilation plates 108 into path 56 so as to press on walls 57 effective to dilate path 56 to enable the removal of isolated tissue mass 52, as shown in FIG. 6B. The arm portions 104 and leg portions 112 are configured in a scissor-like configuration around pivot 110 in the dilation device 102 illustrated in FIGS. 6A and 6B. Thus, an operator holding the dilation device 102 illustrated in FIGS. 6A and 6B can dilate tissue in contact with dilation plates 108 by moving legs portions 112 apart. Distance 120 is larger in FIG. 6B than in FIG. 6A, the leg portions 112 shown in FIG. 6B are shown farther apart than in FIG. 6A.

Figure 7A:
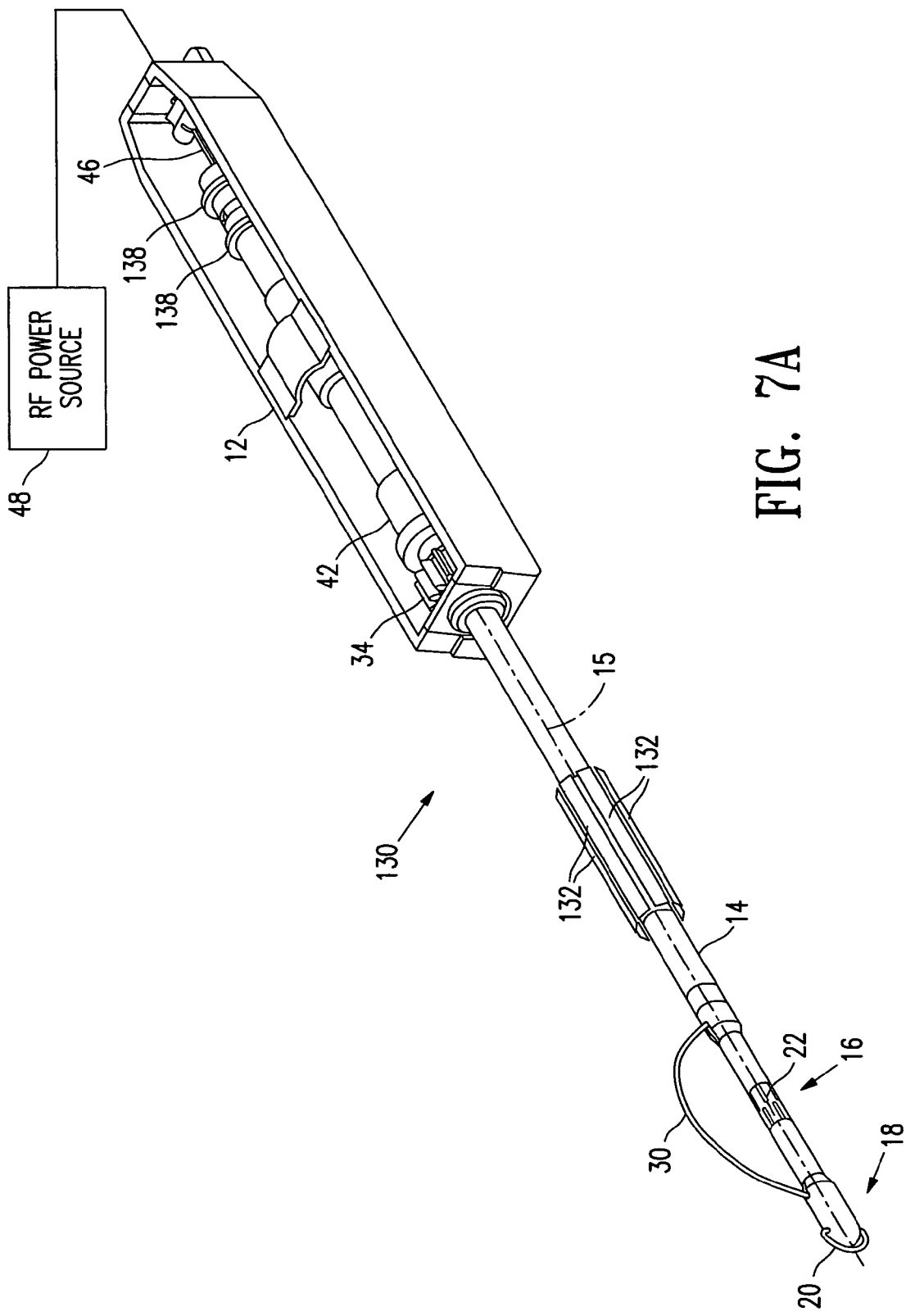
FIG. 7A is a perspective view of a device embodying features of the invention having a plurality of expandable plates, showing the plates in a partially expanded configuration.
Figure 7B:
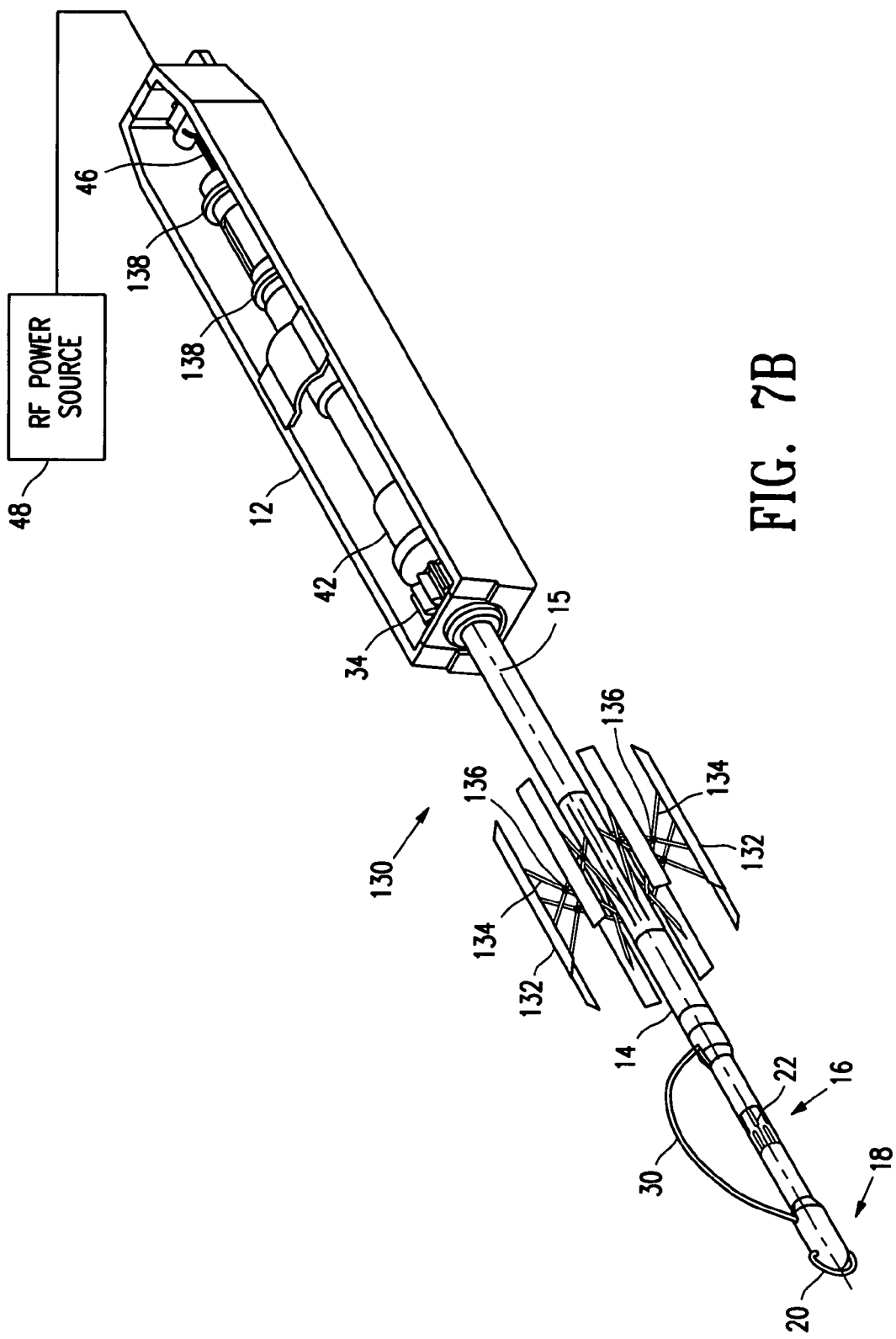
FIG. 7B is a perspective view of the device of FIG. 7A, showing the plates in a maximally expanded configuration.

In embodiments of the invention, devices having other forms of tissue expanders instead of balloons, or in addition to balloons, may be used to dilate a path through tissue. For example, a dilation device 130 embodying features of the invention may have tissue expanders in the form of dilation plates 132 configured to deploy from a retracted position adjacent a shaft 14 to configurations, as shown in FIGS. 7A and B, that are partially expanded (FIG. 7A) and maximally expanded (as shown in FIG. 7B) as deployment struts 134 rotate around pivots 136. Deployment shuttles 138 may be connected by hollow shafts, rods, bands, or other elements housed within shaft 14 to deployment struts 134 so as to move deployment struts 134 in order to deploy and to retract dilation plates 132.

Figure 8A:
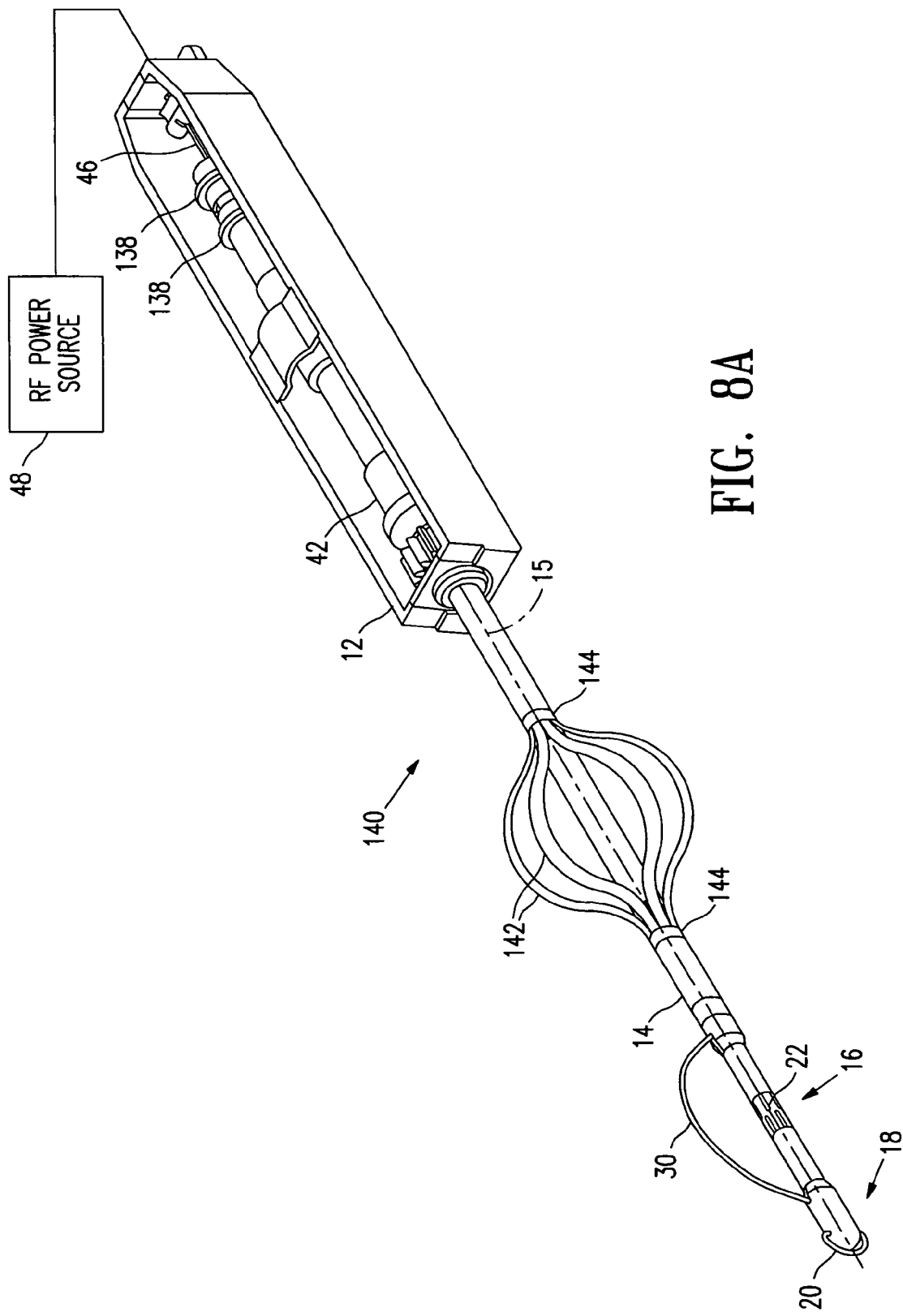
FIG. 8A is a perspective view of a device embodying features of the invention having a plurality of radially expandable bands, showing the bands in an expanded configuration.
Figure 8B:
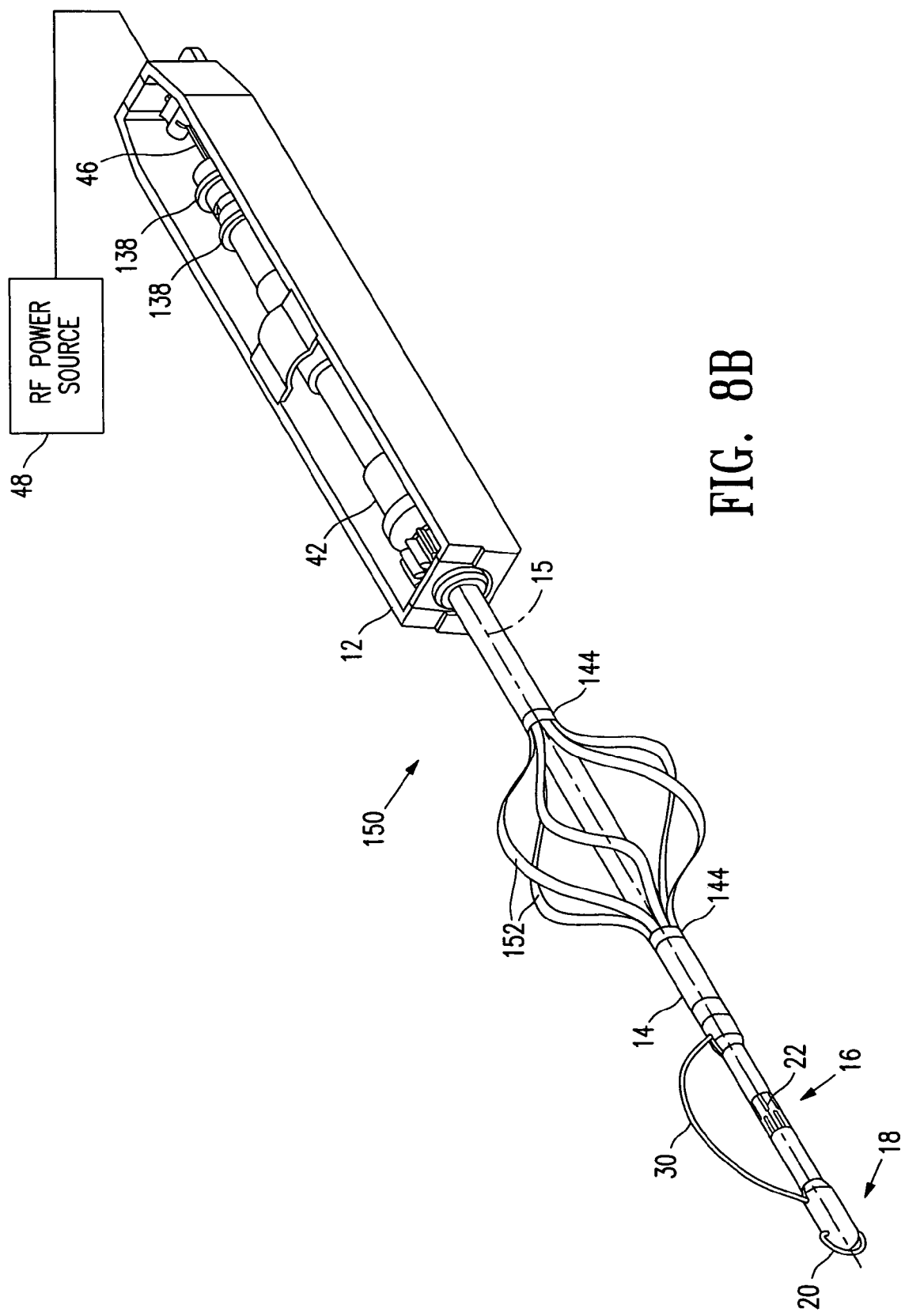
FIG. 8B is a perspective view of a device embodying features of the invention having a plurality of spirally expandable bands, showing the bands in an expanded configuration.
Figure 8C:
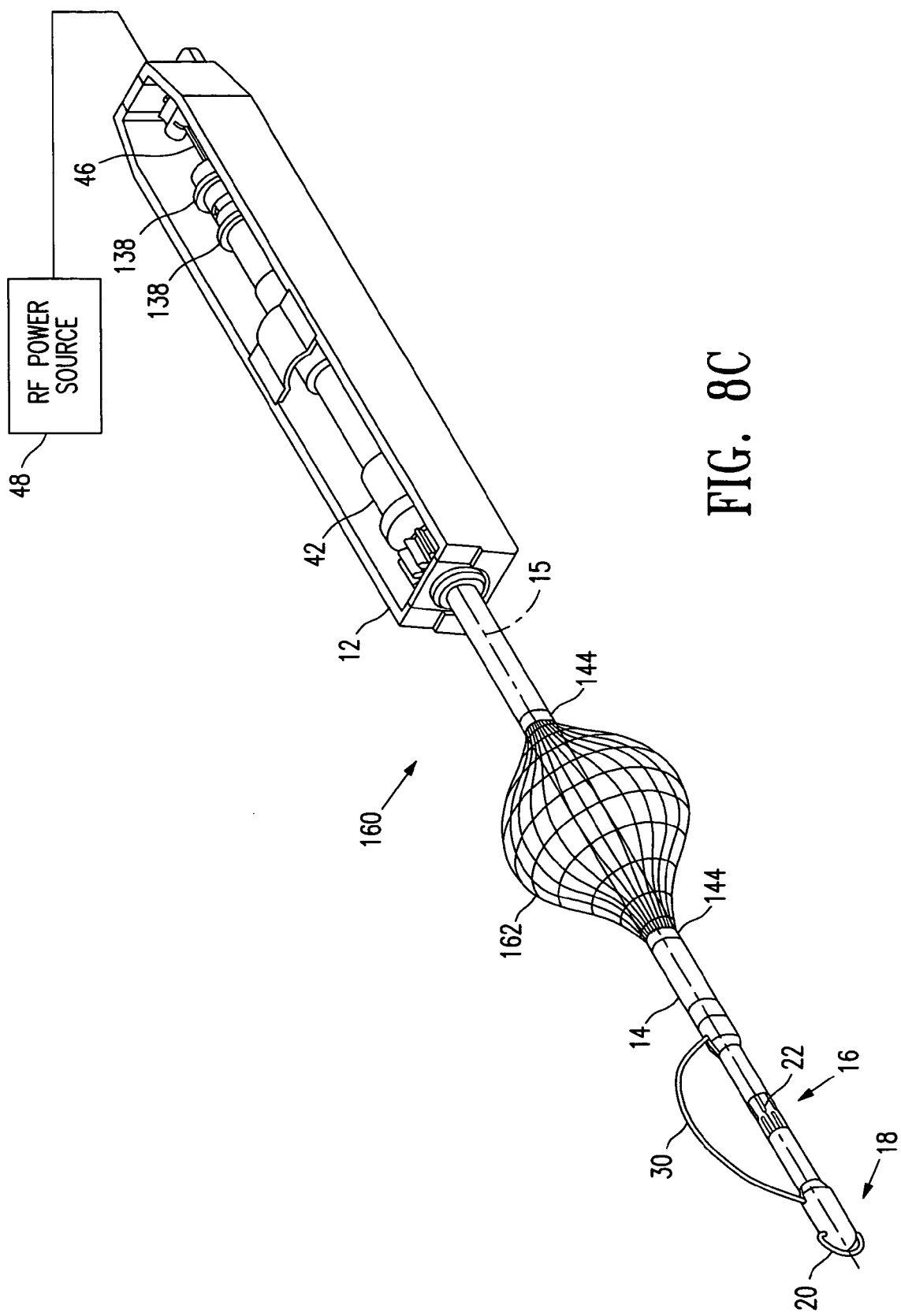
FIG. 8C is a perspective view of a device embodying features of the invention having an expandable meshwork, showing the meshwork in an expanded configuration.

Other examples of devices with tissue expanders are shown in FIGS. 8A-8C. In FIG. 8A, a device 140 with tissue expanders having a plurality of radially expandable bands 142 is shown, with the bands in an expanded configuration spaced radially away from the shaft 14. The bands are effective to contact and to dilate tissue along a tissue path when the bands 142 are deployed to assume an expanded configuration. Collars 144 at the ends of the bands 142 may be moved longitudinally towards each other to effect deployment of the bands 142, and may be moved longitudinally away from each other to effect retraction of the bands 142. Movement of expandable bands 142 may be effected by, e.g., movement of deployment shuttles 138 that are connected by hollow shafts, rods, bands, or other elements housed within shaft 14 to collars 144. In FIG. 8B, a device 150 with tissue expanders is illustrated having a plurality of spirally expandable bands 152. The spirally expandable bands 152 are shown in an expanded configuration spaced away from the shaft 14. The spirally expandable bands 152 are effective to contact and to dilate tissue along a tissue path when the spiral bands 152 are deployed to assume an expanded configuration. The spirally expandable bands 152 may be deployed by movement of a collar 144 or of collars 144, where such movement may be rotational movement around the longitudinal axis 15 of shaft 14, longitudinal movement along the longitudinal axis 15 of shaft 14, or a combination of such movements. FIG. 8C shows a device 160 with tissue expanders having an expandable meshwork 162, the meshwork 162 being shown in an expanded configuration. The meshwork 162 is effective to contact and to dilate tissue along a tissue path when the meshwork 162 is deployed to assume an expanded configuration. The meshwork 162 may assume a retracted configuration adjacent shaft 14, and may be deployed to dilate a path into an expanded configuration as shown by, e.g., longitudinal movement of collars 144 towards each other along shaft 14.

A method for removing a tissue specimen 52 from a tissue bed 58 within a patient's body is illustrated by FIGS. 3A and 3B. Elongate shaft 14 of device 10 may be inserted into the patient to bring tip 18 near to or through the desired location within a patient's body, with shaft 14 occupying a position within a path 56 leading to the tissue mass that is to be removed. Distal cutting surface 20 may be used to aid in making a path 56 to the desired location within a patient's body and in positioning the device in a desired location. Side cutting surface 30 may be deployed and shaft 14 rotated, thereby rotating the other elements of the device including side cutting surface 30 and causing side cutting surface 30 to cut tissue and to isolate a tissue mass 52 from the surrounding tissue bed 58. Anchoring elements 24 may be deployed from slots 22 to anchor device 10 to the isolated tissue mass 52. Proximal balloon 26 may then be inflated by fluid flow through inflation tube 28, pressing on path walls 57 and expanding the diameter of the path 56, aiding in the removal of the isolated tissue mass 52. In preferred embodiments, distal cutting surface 20 and/or side cutting surface 30 may be provided with electrical power, such as RF power, and used as electrosurgical cutting elements.

Another method for removing a tissue specimen 52 from a tissue bed 58, using a device 10 having two balloons 26 and 50, is illustrated by FIGS. 4A-4C. In use during a diagnostic or therapeutic procedure to remove a tissue mass 52 from a patient, the sequence of inflation of balloons 26 and 50 would follow the sequence shown in FIGS. 2A, 2B and 2C. Thus, following insertion of the device 10 into the patient to bring tip 18 near to or through the desired location within a patient's body, side cutting surface 30 may be deployed and shaft 14 rotated, causing side cutting surface 30 to cut tissue and to isolate a tissue mass from the surrounding tissue bed. Anchoring elements 24 may be deployed from slots 22 to anchor device 10 to the isolated tissue mass. Proximal balloon 26 may then be inflated, pressing on path walls 57 and expanding the diameter of the path 56. The expanded path 56 may more easily accommodate the removal of the isolated tissue mass 52. Distal balloon 50 may next be inflated by fluid flow via inflation tube 51, pressing on tissue and urging the device 10 and attached tissue mass 52 out along the path 56, further aiding in the removal of the isolated tissue mass 52. In preferred embodiments, and as illustrated in FIGS. 2A-2G, distal cutting surface 20 and side cutting surface 30 may be provided with electrical power, such as RF power from a RF power source 48, and used as electrosurgical cutting elements.

In preferred embodiments, the distal cutting surface 20 and side cutting surface 30 are electrosurgical cutting surfaces. Power to these cutting surfaces may be from any suitable source of electrical power, preferably a source of RF power 48. In one embodiment of the invention, the source of RF power 48 can operate at frequencies from about 200 kiloHertz (kHz) to about 10 megaHertz (MHz). Preferably, side cutting electrode 30 receives RF power at a frequency of, for example, between about 2.5 MHz and about 7.5 MHz, preferably at a frequency of about 5 MHz, at a voltage of between about 450V to about 550V and at a power of up to about 400 Watts (W). In embodiments of the invention, a distal cutting surface receives RF power at a frequency of about 300 kHz to about 1.5 MHz, preferably about 500 kHz to about 1000 kHz, more preferably about 700 kHz to about 900 kHz, at a power of, for example, between about 50 W to about 150 W, and more specifically, at a power of from about 80 W to about 100 W. The distal cutting surface and side cutting surface are also effective to cauterize tissue when sufficient amounts of power (typically greater than the amounts listed above) are supplied to them. Examples of suitable power sources are disclosed in co-owned, co-pending U.S. patent application Ser. No. 09/752,978, filed Dec. 28, 2000, the disclosure of which is hereby incorporated by reference in its entirety.

Devices 10, 130, 140, 150, 160 and devices 102 of the invention may be used together for removing a tissue specimen from a tissue bed within a patient's body. Thus, one embodiment of a method for removing a tissue specimen includes the steps of positioning a device 10 as illustrated in FIGS. 1-4, having a shaft 14 with an inflatable balloon 26 adjacent a tissue specimen 52 along a path 57 in a tissue bed 58 within a patient's body; enclosing a portion of the shaft 14 with a portion of a dilation device 102 as illustrated in FIGS. 5 and 6; inflating a balloon 26 effective to dilate the path 56 through the tissue bed 58; enlarging the transverse dimension of the dilating device 102, as by manipulating the arms 104 having dilation plates 106 to separate the legs 112 of the dilating device 102, effective to dilate a path 56 through the tissue bed 58; and removing said tissue specimen 52.

Balloons may be made from any suitable material or materials, including polymers, rubber (both natural and synthetic such as latex and silicon rubber). For example, balloons may be made from polymers and polymer blends, including polymers such as polyamides, polyesters, polyethylene, polyimides, polytetrafluoroethylene (Teflon®), polyurethane, polyvinyl chloride, polynitrile, polyethylene terephthalate and polyolefin polymers. Balloons may be made from flexible and foldable materials such as woven material, braided material, knit material, web material, mesh material, film material, flexible laminate material; and/or elastic material.

Balloons may be inflated by increasing internal pressure within the balloon, as by flow of a fluid into the balloon to fill and expand the balloon. The fluid may be a gas or liquid. In one embodiment, a balloon and balloon inflation tube is connected by a conduit to a syringe filled with a liquid, such as water, saline, mineral oil, or other substantially incompressible liquid. Pressure on the plunger of the syringe forcing the fluid out of the syringe, through the conduit, and into the balloon is effective to inflate the balloon. The conduit may be a flexible tube, such as one made from Tygon® tubing, and may pass through a valve or be fitted with a clip or clamp. Closure of a valve or clamp or placement of a clip onto the conduit, such as a dialysis clip, is effective to prevent fluid flow after inflation of the balloon so as to maintain the balloon in an inflated configuration as long as is desired. Alternatively, a balloon may be connected to a source of high pressure air or gas, and may be inflated by allowing air or gas into the balloon until a desired amount of inflation and internal pressure has been achieved.

Dilation devices embodying features of the invention may be made from any suitable material, including metals, composites, plastics, and ceramics. For example, devices 102 embodying features of the invention may be made stainless steel, which may be coated with a biocompatible material, or from a biocompatible polymer, composite, such as a glass-reinforced nylon, high density polyethtlene (HDPE), or other durable material. Devices 10, 130, 140, 150, and 160 may similarly be made from any suitable material, including metals, composites, plastics, ceramics, and combinations of such materials, and are typically made from more than a single material.

Preferably, the devices embodying features of the invention are made from materials that are suitable for sterilization, including ultraviolet, chemical and radiation sterilization. Such sterilizable materials include stainless steel and other metals, ceramics, composites, plastics, and such polymers as polyethylene, polypropylene, a fluorinated ethylene polymer, or other material.

Devices embodying features of the invention may also include other useful features that may aid placement or removal of tissue masses from within a patient. For example, markings 31, as shown in FIG. 1A, may be placed along shaft 14 of a device 10, 130, 140, 150 or 160 to aid an operator in determining the depth of tip 18. Other useful features may be included in a device 10, 102, 130, 140, 150, 160, or other devices and systems embodying features of the invention. Thus, while particular forms of the invention have been illustrated and described, it will be apparent that various modifications can be made without departing from the spirit and scope of the invention. Accordingly, it is not intended that the invention be limited, except as by the appended claims. Reference to the terms "members," "elements," "sections," "expanders," and terms of similar import in the claims which follow shall not be interpreted to invoke the provisions of 35 U.S.C. §112(paragraph 6) unless reference is expressly made to the term "means" followed by an intended function.

What is claimed is:

1. A method of separating a tissue specimen from a target site within a patient's body and removing the tissue specimen through a passageway leading to the target site from a location exterior to the patient's body, comprising:
   a. providing a biopsy device comprising an elongated shaft with a tissue penetrating distal tip, a distal shaft portion proximal to the distal tip, a tissue cutting member on the distal shaft portion and a tissue securing member on the distal shaft portion;
   b. providing a tissue expander configured to be slidably disposed about the distal shaft portion with a distal end proximal to the tissue cutting member, the tissue expander comprising first and second expansion member having elongated handles with operable distal ends, manually manipulatable proximal ends, tissue expanding elements on the distal ends thereof having an exterior configured to fit into the passageway leading to the target site and a finger grip on the proximal end and the first and the second expansion members being pivotally connected;
   c. advancing the biopsy device through the passageway until the distal shaft portion of the biopsy device is located at the target site;
   d. separating the tissue specimen from tissue at the target site by the tissue cutting member on the biopsy device;
   e. securing the separated tissue specimen to an exterior of the distal shaft portion of the biopsy device with the tissue securing member;
   f. positioning the tissue expanding elements of the tissue expander proximally adjacent to the tissue cutting member;
   g. expanding the tissue expanding elements so as to expand the passageway formed by the tissue penetrating distal tip; and
   h. withdrawing the biopsy device and the tissue specimen secured thereto through the expanded passageway formed by the tissue expander, wherein the tissue expander is in an expanded configuration and the distal end of the tissue expander is positioned proximal to the tissue cutting member as the biopsy device is being withdrawn.

* * * * *